United States Patent [19]

Bruice

[11] Patent Number: 5,202,317
[45] Date of Patent: Apr. 13, 1993

[54] SYNTHETIC DRUG MOLECULES THAT MIMIC METALLOENZYMES

[75] Inventor: Thomas C. Bruice, Santa Barbara, Calif.

[73] Assignee: The Regents of the University of California, Berkeley, Calif.

[21] Appl. No.: 582,626

[22] Filed: Sep. 13, 1990

[51] Int. Cl.$^5$ .............. A61K 31/40; E07D 487/22
[52] U.S. Cl. ..................................... 514/185; 540/145
[58] Field of Search ........................ 514/185; 540/145

[56] References Cited

U.S. PATENT DOCUMENTS 4,029,819  6/1977  Michelson .............................. 426/61
4,129,644  12/1978  Kalopissis ............................ 424/59
4,695,456  12/1987  Wilder .................................. 424/94.5

FOREIGN PATENT DOCUMENTS 0138111  4/1985  European Pat. Off. .
3626159  2/1988  Fed. Rep. of Germany ...... 540/145
3079887  4/1988  Japan ................................. 540/145

OTHER PUBLICATIONS

Miyamoto et al.; Bull. Chem. Soc. Jpn. 60, 1649-59 1987.
Bruice, in *Mechanistic Principles of Enzyme Activity*, J. F. Liebman et al., eds. (VCH Publishers, Inc. New York) 1988, pp. 227-277.
Bucks et al., *J. Am. Chem. Soc.* (1982) 104:340-343.
Collman et al., *Proc. Natl. Acad. Sci.* (1977) 74:18-22.
Collman et al., in *Organic Synthesis Today and Tomorrow*, B. M. Trost et al., eds. (Permagon Press, Oxford), 1981, pp. 29-45.
Collman et al., *J. Am. Chem. Soc. (1990) 112:166-173*.
Dolphin et al., *Heterocycles* (1981) 16:417-447.
Donohoe et al., *J. Am. Chem. Soc.* (1988) 110:6119-6124.
Kagan et al., *J. Am. Chem. Soc.* (1977) 99:5484-5486.
Kim et al., *J. Am. Chem. Soc. (1988) 110:4242-4246*.
Proniewiczs et al., *J. Am. Chem. Soc.* (1989) 111:2105-2110.
Ward et al., *J. Am. Chem. Soc. (1981) 103:5236-5238*.
Hallewell et al., *Nucleic Acids Res.* (1985) 13(6):2017-2034.

Primary Examiner—Mukund J. Shah
Assistant Examiner—Y. N. Gupta
Attorney, Agent, or Firm—Morrison & Foerster

[57] ABSTRACT

Synthetic enzymes that mimic the catalytic activity of naturally occurring enzymes by providing catalytic sites enclosed in cages that protect the sites from undesirable molecules and attract and permit entry of the relevant substrates are disclosed. Molecules that mimics the catalytic activity of superoxide dismutase and catalase, pharmaceutical compositions containing these molecules, and methods for using these compositions are also disclosed.

31 Claims, 14 Drawing Sheets

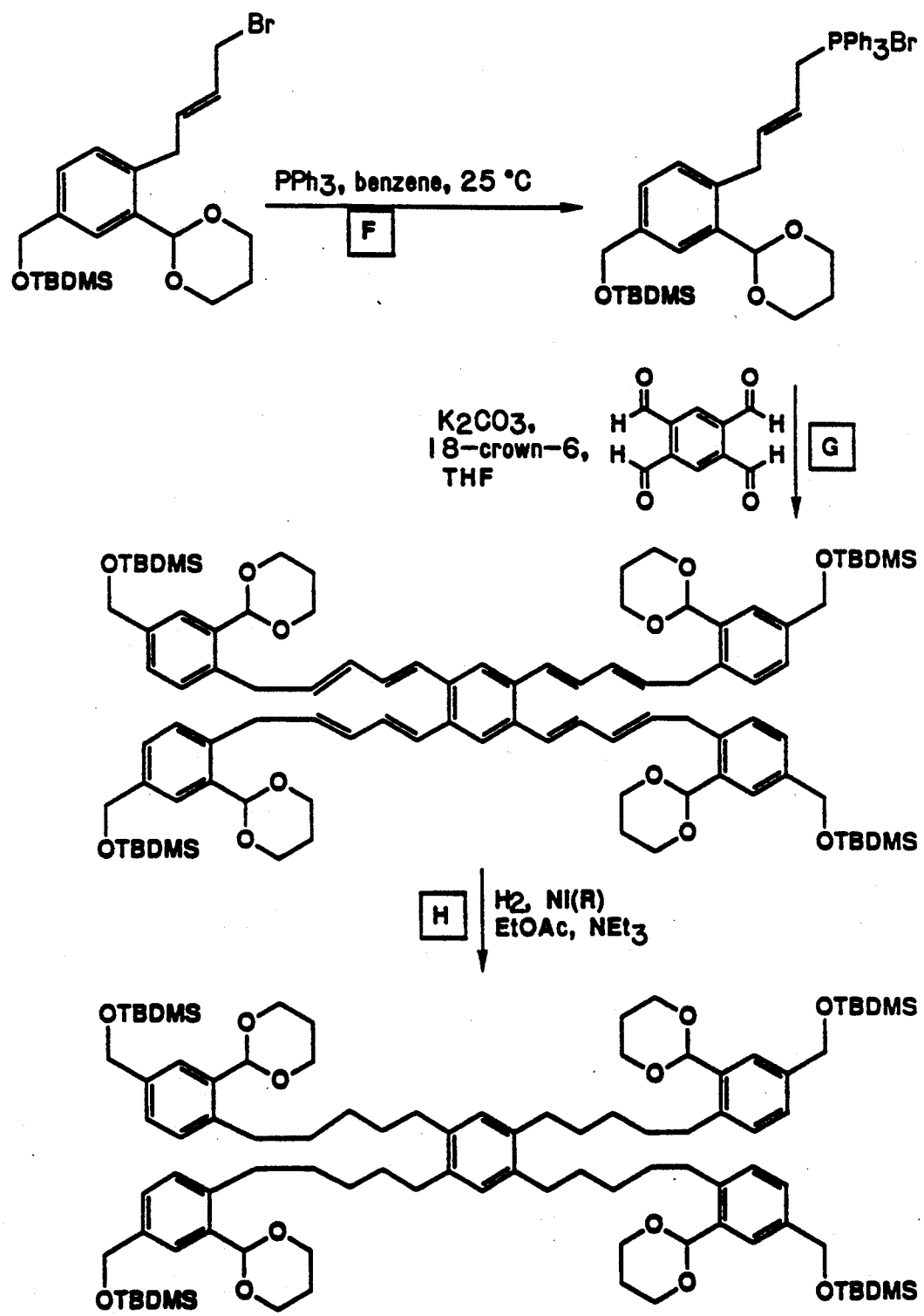
FIG. IA

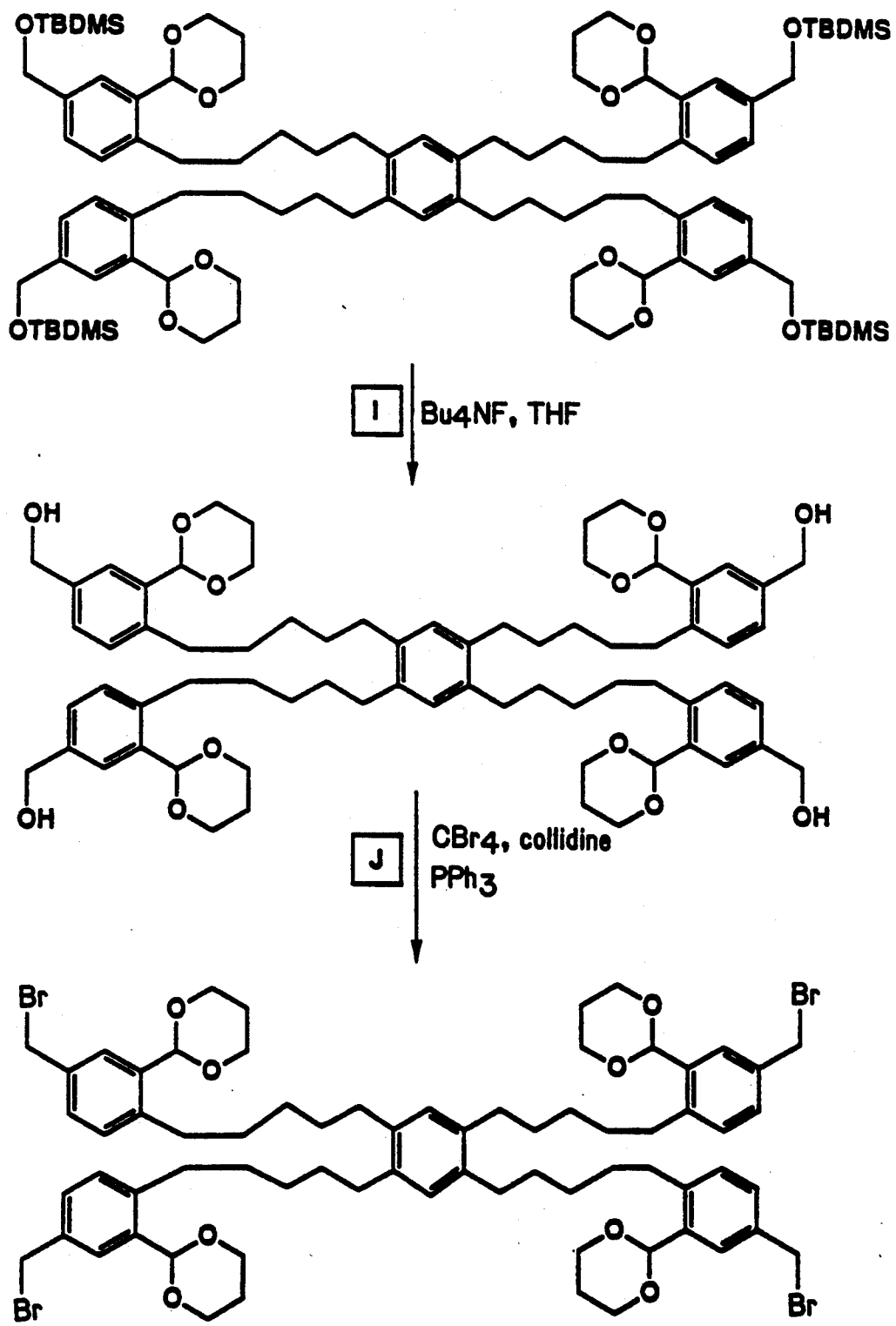
FIG. IB

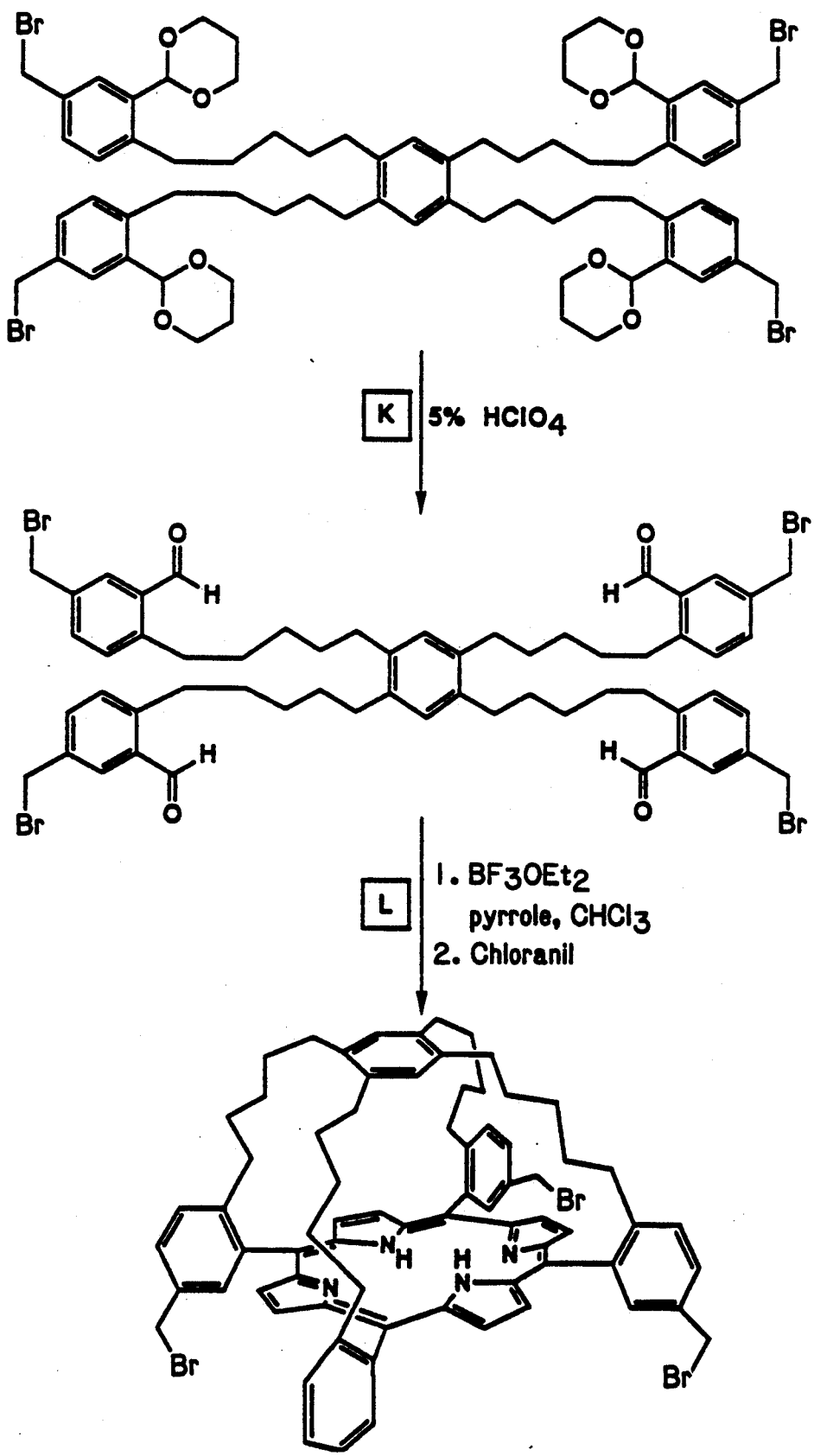
FIG. IC

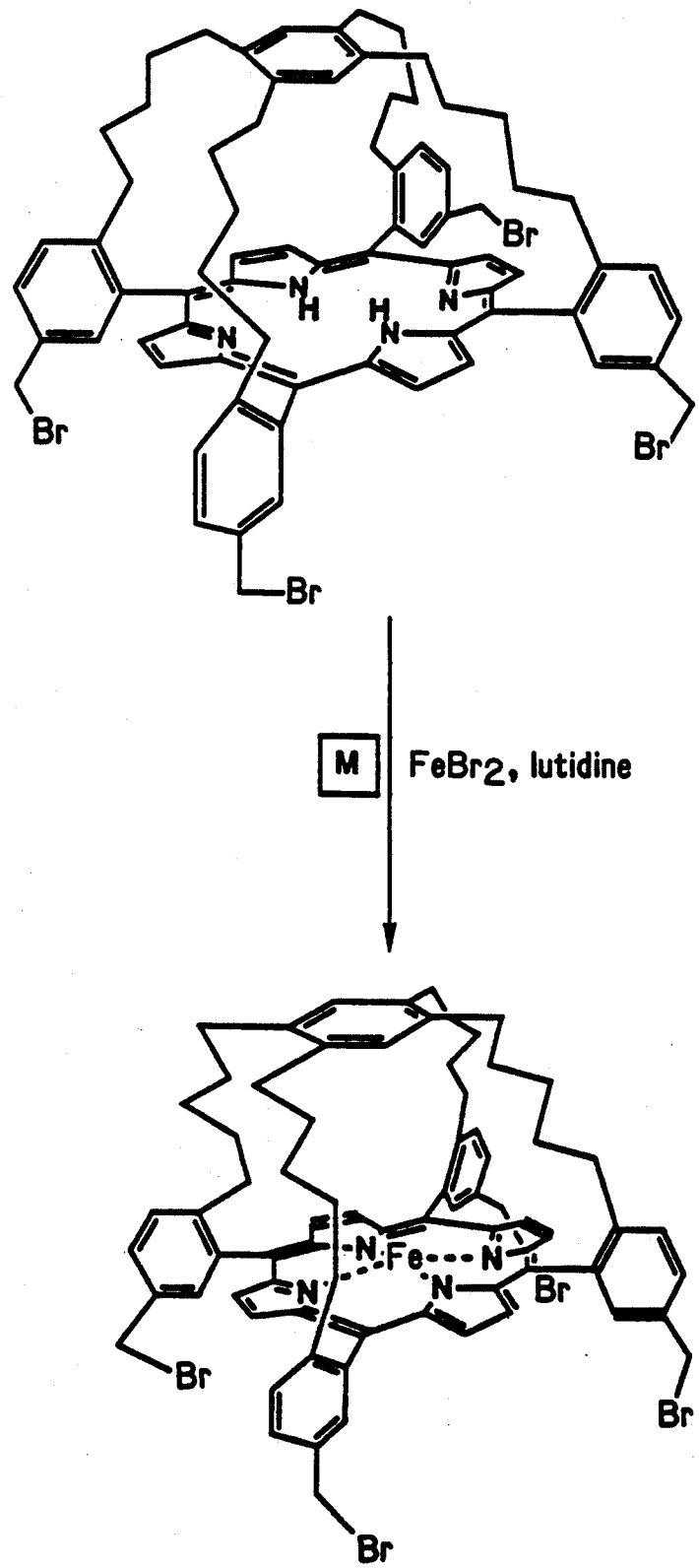
FIG. ID

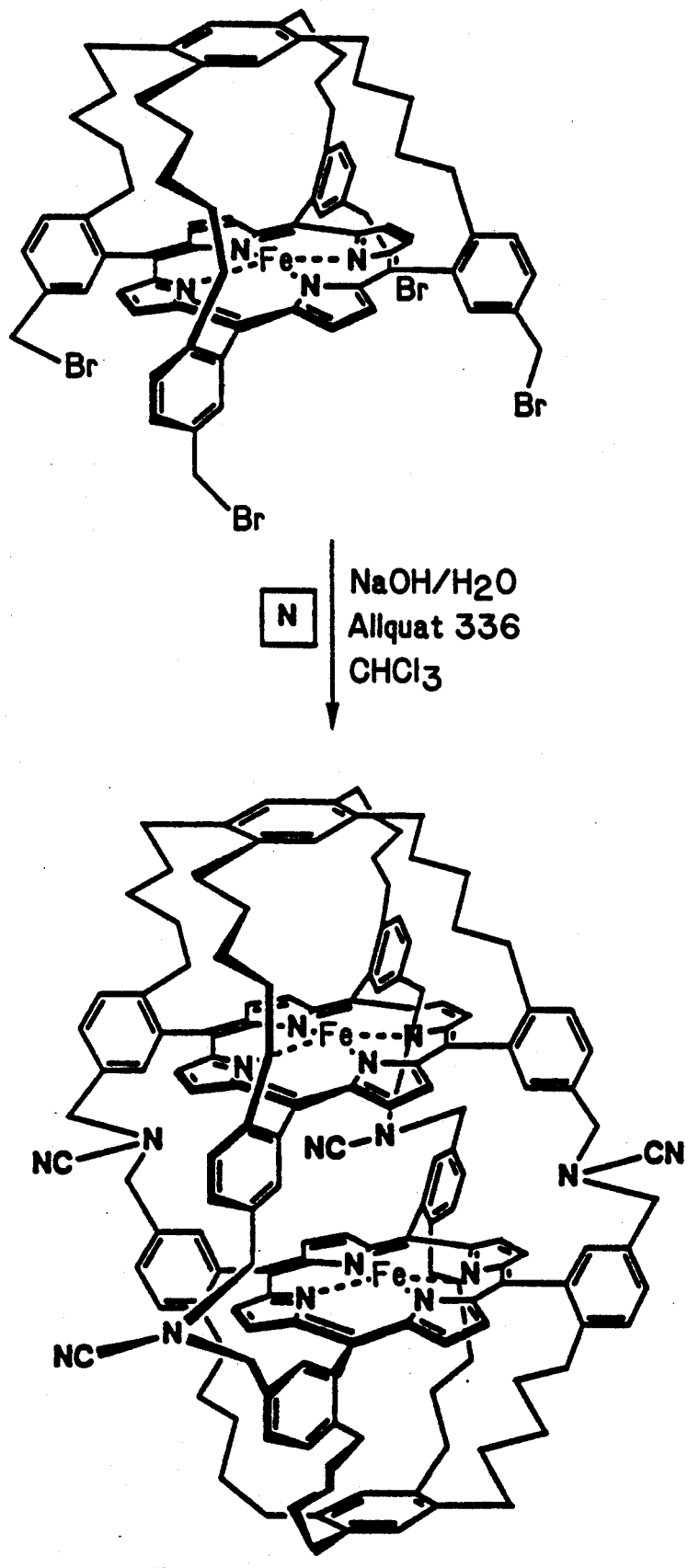
FIG. IE

3a, R=Ts
3b, R=H
3c, R=CN

12a. M = H$_2$
b. M = Zn

13a. M = Zn
b. M = H$_2$

SYNTHESIS OF TETRAKIS (PENTAMETHYLENE) CAPPED PORPHYRIN

SYNTHETIC DRUG MOLECULES THAT MIMIC METALLOENZYMES

TECHNICAL FIELD

This invention is in the field of synthetic drug molecules that mimic the functions of naturally occurring enzymes. More particularly, it relates to molecules that mimic the catalytic activity of metalloenzymes such as superoxide dismutase and catalase by providing an active site accessible only to the relevant enzyme substrates.

BACKGROUND ART

Metabolic reactions in response to molecular oxygen can produce harmful reactive oxygen species such as the superoxide ion ($O_2^-$), hydrogen peroxide or hydroperoxide ion ($H_2O_2$ or $^-OOH$), or hypochlorite ion ($ClO^-$). For example, reactive oxygen species are produced by uncontrolled activated neutrophils at inflammation sites in the human body. Patients with myocardial ischemia can suffer irreparable tissue damage due to the production of $H_2O_2$ or $O_2^-$. This effect is also found in and may be causally related to rheumatoid arthritis. Reactive oxygen species are also implicated in carcinogenesis.

A number of naturally occurring enzymes aid in the decomposition of harmful reactive oxidants. Superoxide dismutase (SOD) denotes a family of metalloenzymes that catalyze, among other reactions, the dismutation of superoxide ions according to the following equation:

$$2O_2^- + 2H^+ \rightarrow H_2O_2 + O_2.$$

The still-harmful SOD reaction product, hydrogen peroxide, is subject to further dismutation by the enzyme catalase according to this equation:

$$2H_2O_2 \rightarrow 2H_2O + O_2.$$

Thus, SOD and catalase together catalyze the overall dismutation of superoxide to water and oxygen, and form an important part of an organism's self-protective system against reactive oxidants.

Enzymes of the SOD family have many important uses. U.S. Pat. No. 4,029,819 to Michelson teaches the use of SOD as a foodstuff additive and preservative for the prevention of oxidation and auto-oxidation of lipids. U.S. Pat. No. 4,129,644 to Kalopissis et al. teaches the application of SOD to protect skin and maintain the integrity of the natural keratinic structure of skin and hair. The usefulness of SOD in alleviating skin irritation and inflammation is demonstrated in U.S. Pat. No. 4,695,456 to Wilder. SOD may also be used as a general anti-inflammatory, and as an attenuator to be applied after exposure to superoxide ion-generating agents such as radiation or paraquat, as described in European Patent Application No. 84111416.8 to Hallewell et al.

The catalytic activity of SOD and catalase, and many other metabolic enzymes in biological systems, requires the presence of one or more metal ligands at the catalytic site. Covalently linked cofacial- ("strati-") bisporphyrins and their metal complexes have been employed as models for these multimetal proteins. See, e.g., D. Dolphin et al., *Heterocycles* (1981) 16:417. Extensive studies have been carried out on the four electron reduction of $O_2$ to water as a model for cytochrome-c oxidase using cofacial-bisporphyrins with relatively small internal cavities. L. M. Proniewicz et al., *J. Am. Chem. Soc.* (1989) 111:2105; K. Kim et al., *J. Am. Chem. Soc.* (1988) 110:4242. Cofacial-bisporphyrins have also been employed as models for the energy storage and electron transfer of the photosynthetic reaction center as well as for carbon monoxide and dioxygen binding affinity of hemoglobin and myoglobin. R. R. Bucks et al., *J. Am. Chem. Soc.* (1982) 104:340; B. Ward et al., *J. Am. Chem. Soc.* (198) 103:5236. The cofacial-bisporphyrins may also serve as models or substitutes for multimetal proteins such as cytochrome-$c_3$ and nitrogenase, as well as mixed function oxidases, metallo-sandwich complexes, metal-metal multiple bonds and even anticancer drugs. T. C. Bruice in *Mechanistic Principles of Enzyme Activity.* pp. 227–277, J. F. Liebman et al., eds., VCH Publishers, Inc., New York (1988); R. J. Donohoe et al., *J. Am. Chem. Soc.* (1988) 110:6119; J. P. Collman et al., *J. Am. Chem. Soc.* (1990) 112:166. Advances in the synthesis of cofacial-bisporphyrins of fixed geometry will aid in the understanding of a multitude of biological and physical phenomena.

Currently used cofacial-bisporphyrin dimers are linked together by two bridges at transoid β-positions of the porphyrin rings. The bridges contain amide or ester linkages that are the condensation products of acid chloride monomers with other monomers containing amine or alcohol side chains, under high dilution conditions, with yields ranging from 30–60%. These doubly-bridged molecules have a flexibility that allows the porphyrin rings to assume an undesirable offset geometry. $^1H$ NMR studies show that in solution at room temperature, these molecules exist in a number of conformational isomers. J. P. Collman et al. in *Organic Synthesis Today and Tomorrow*, pp. 29–45, B. M. Trost et al., eds., Pergamon Press, Oxford (1981). Moreover, when the bridge length is decreased to four atoms or less in the doubly-bridged systems, the porphyrins are held within π-π-interaction distance of each other and remain rigidly eclipsed. K. Kim et al., *J. Am. Chem. Soc.* (1988) 110:4242.

Most cofacial-bisporphyrins also have unsubstituted meso-positions, making them susceptible to oxidation. Phenyl groups substituted at all four meso-positions of the porphyrin ring can be used to increase oxidation resistance. However, the synthesis of covalently-linked cofacial-bis-5, 10, 15, 20-tetraphenylporphyrins, ("R-(TPPH$_2$)$_2$s"), with relatively small internal cavities has been difficult, if not impossible. J. P. Collman et al., *Proc. Natl. Acad. Sci. USA* (1977) 74:18. With the exception of the elegant work of Kagan, R-(TPPH$_2$)$_2$s wherein the porphyrin rings are linked by four bridges and separated by less than 7 angstroms are unknown. N. E. Kagan et al., *J. Am. Chem. Soc.* (1977) 99:5484.

Finally, cofacial-bisporphyrins have an additional drawback when used as model enzymes: reactants can approach the metal ligands from either face of the ring system. Although interfacial access can be limited by cavity size, it has until now been difficult to control extrafacial access to the metal ligands.

SUMMARY OF INVENTION

An improvement in strati-bisporphyrin systems that mimic the catalytic function of monometallo- or dimetallo-enzymes has now been found. In accord with this invention, a molecule is synthesized wherein a catalytic cofacial-bisporphyrin system is fixed within a cage that protects the catalytic site from undesirable biomolecules while permitting entry of the relevant substrates. The cage consists of multiple bridging units with well-defined bridging lengths, and two capping groups that block undesirable biomolecules from the catalytic site. The bridging units are capable of introducing functional concentrating groups to attract the enzyme substrate to the catalytic site.

The improvement of this invention, in addition to enabling the mimicry of native enzymes, also enables the creation of synthetic enzymes that catalyze new reactions or combine the activities of two or more enzymes. More specifically, this invention permits the synthesis of a synthetic enzyme that has the catalytic activities of both superoxide dismutase and catalase, in addition to catalyzing the conversion of hypochlorite to chloride. This synthetic enzyme, by catalyzing two reactions at one site, is superior to the natural SOD/catalase system that exposes the organism to free reactive hydrogen peroxide during the two-step breakdown. The synthetic enzyme, by breaking down superoxide, hydroperoxide and hypochlorite anions, destroys potential cancer-causing oxygen species.

It is thus an object of this invention to provide a bisporphyrin system designed to catalyze metalloenzyme reactions such as the superoxide dismutase and catalase reactions. The bisporphyrin system is doubly-capped to form a "bis-spheroidal porphyrin" structure. In a preferred embodiment, the system also includes charged groups covalently linked to each bridging unit to attract the desired reactants.

It is a further object of this invention to provide a bisporphyrin system as described above designed to catalyze both the superoxide dismutase and catalase reactions. In a preferred embodiment of the SOD/catalase mimic, two porphyrin systems are linked by four three-atom-length bridging units, thereby affording rigidity and geometry narrowly defining the cavity size between the rings to be in the range of 4 to 7 angstroms, and only permitting the entry of desired reactants. In the most-preferred embodiment, the mimic includes positively charged guanido groups covalently linked to each bridging unit to attract the desired reactants.

It is another object of this invention to provide compositions and methods for treatment of inflammation in human patients by administering an effective amount of a bisporphyrin system that catalyzes the superoxide dismutase and catalase reactions, as well as the decomposition of hypochlorite to chloride.

It is yet another object of this invention to provide compositions and methods for reducing the level of cancer-causing oxygen species in human patients by administering an effective amount of a synthetic bisporphyrin system that catalyzes both the superoxide dismutase and catalase reactions as well as the decomposition of hypochlorite to chloride.

Additional objects, advantages and novel features of the invention will be set forth in part in the description which follows, and in part will become apparent to those skilled in the art upon examination of the following, or may be learned by practice of the invention.

In one aspect of the invention, a synthetic catalyst for biological reactants is provided consisting of a catalytic site enclosed in a cage. The catalytic site includes: two quasi-planar $\pi$-conjugated ring systems, each of which has an interfacial and extrafacial plane, and each of which is capable of chelating a metal ligand; and two metal ligands, each of which is chelated by one of the ring systems. The cage includes: at least two bridging units, each of which is covalently linked to the two ring systems, so that the ring systems are fixed at an interfacial plane separation which permits entry of the biological reactants between the ring systems; two capping groups, each of which is situated on the extrafacial plane side of one of the ring systems, and each of which is attached to the ring systems through at least one direct or indirect covalent linkage, so that extrafacial access to the ring systems for naturally occurring biological molecules is barred; and optionally includes one or more concentrating groups covalently linked to the bridging units, the concentrating groups possessing a charge opposing that of the biological reactants.

In another aspect of the invention, a pharmaceutical composition for the reduction of inflammation is provided, wherein that composition contains an effective inflammation-reducing amount of a synthetic bisporphyrin system that catalyzes both the superoxide dismutase and catalase reactions as well as the decomposition of hypochlorite to chloride, and a pharmaceutically acceptable carrier.

In yet another aspect of the invention, a method for the prevention and treatment of inflammation is provided, wherein that method consists of administering to a patient in need of such treatment an effective amount of a synthetic bisporphyrin system that catalyzes both the superoxide dismutase and catalase reactions as well as the decomposition of hypochlorite to chloride, and a pharmaceutically acceptable carrier.

In still another aspect of the invention, a method for reducing the level of cancer-causing oxygen species in a patient is provided, wherein that method consists of administering to a patient an effective amount of a synthetic bisporphyrin system that catalyzes both the superoxide dismutase and catalase reactions as well as the decomposition of hypochlorite to chloride, and a pharmaceutically acceptable carrier.

DETAILED DESCRIPTION OF THE INVENTION

Figure 1:
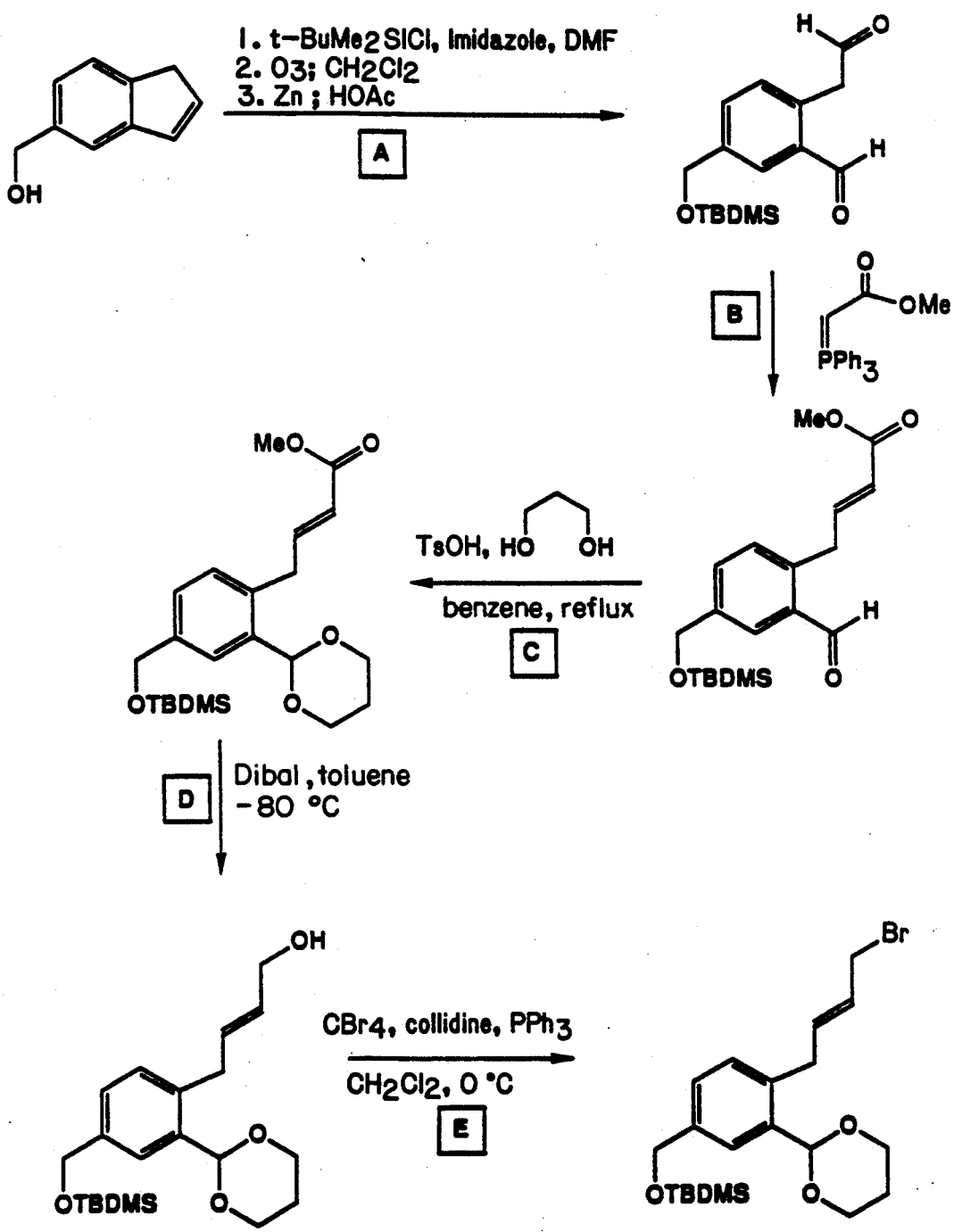
FIG. 1 shows steps for the synthesis of a catalyst that mimics the roles of SOD and catalase.
Figure 1F:
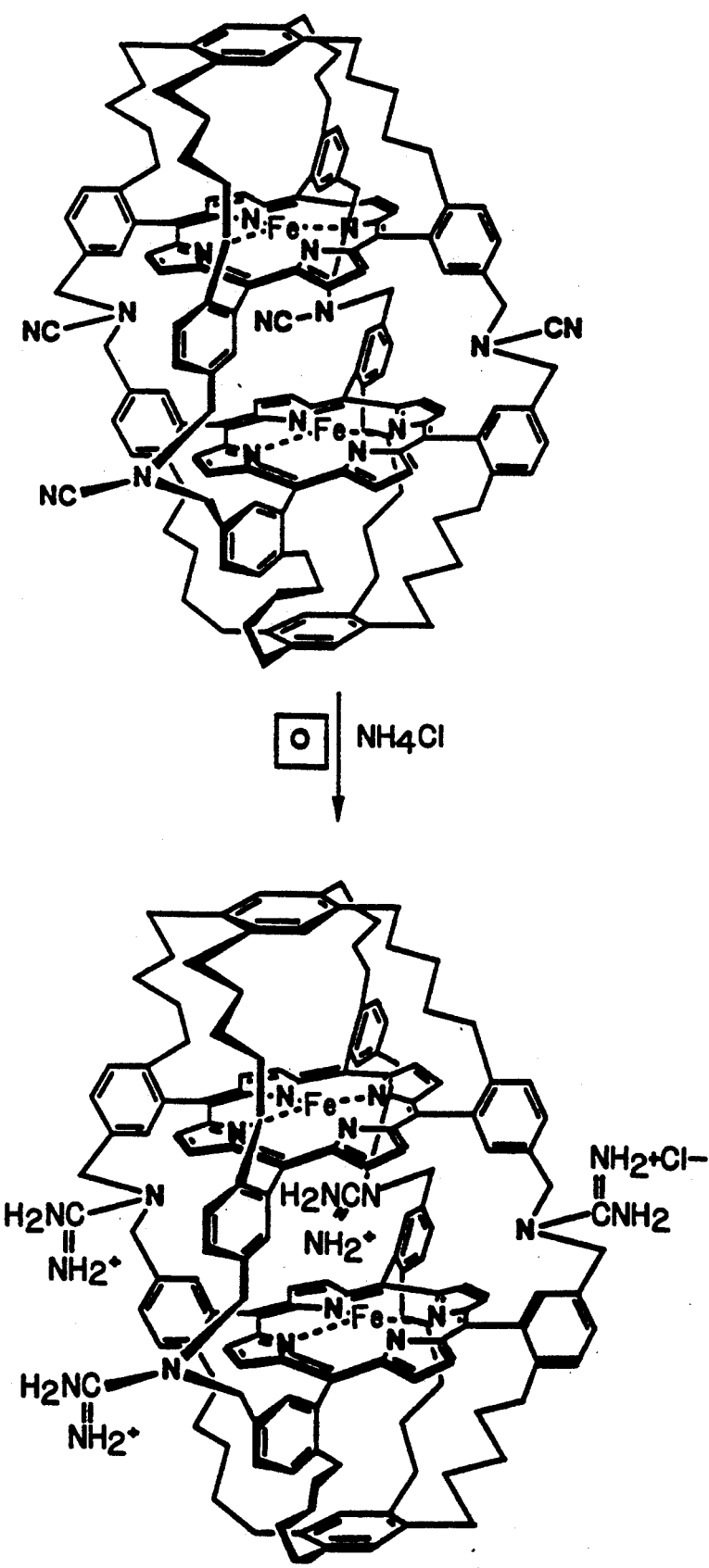

Definitions:

A "quasi-planar $\pi$-conjugated ring system" as used herein refers to planar or quasi-planar aromatic ring compounds having alternating adjacent $\pi$-bonds. The ring system may be mononuclear aromatics or heterocyclic aromatics, such as benzene derivatives, pyrrole, furan, thiophene, imidazole, oxazole, thiazole, pyrazole, pyridine, or pyrimidine derivatives, or polynuclear fused systems such as naphthalene or azulene derivatives, or polynuclear fused heterocycles such as purine, quinoline, isoquinoline, or carbazole derivatives and the like. The ring system may also include polynuclear systems such as the tetrapyrroles, including porphyrin derivatives. The ring systems may be substituted at one or more locations.

The "porphyrins" of this invention are derivatives of the tetrapyrrole compound porphin. Porphyrins as used herein include side-chain substituted porphins, such as etioporphyrins, mesoporphyrins, uroporphyrins, coproporphyrins and protoporphyrins. The porphyrins of this invention are $\pi$-conjugated ring systems, and are quadridentate chelating complexes capable of chelating metals in a heme-like structure.

"Strati-porphyrins" or "cofacial-porphyrins" as used herein describe the orientation of one porphyrin ring in a parallel or nearly-parallel plane directly atop another.

"Bridging units" as used herein refer to divalent organic and substituted organic chains capable of joining two π-conjugated ring systems through covalent linkages.

"Capping groups" as used herein refer to any organic or substituted organic moiety capable of being covalently linked to one side of a π-conjugated ring system, thereby preventing biomolecular access to that side of the system.

"Concentrating groups" as used herein refer to any charged organic or substituted organic moiety of 5 carbons or less. The concentrating groups are attached to the bridging units at the entry to the cavity of the catalyst. By designing the concentrating groups to have a charge opposite that of the biological reactants for the catalyst, the concentrating groups will have the effect of attracting the reactants toward the cavity site for catalysis.

The Catalyst:

There are five linked components that constitute the catalysts of this invention. Two components provide the catalytic site: (1) the quasi-planar π-conjugated ring systems; and (2) the metal ligands chelated by the ring systems. The remaining components constitute the cage that protects the catalytic site and attracts the relevant substrates: (3) the bridging units that link the ring systems; (4) the capping groups that shield the metal ligands from the outside environment; and (5) the concentrating groups that attract the substrates for the catalyst.

It will be seen that the three "cage" components could also be used to protect catalytic sites other than chelated metal ligands and thereby provide a broad range of synthetic enzymes. For example, the caged catalytic site could mimic the structure of a serine protease, or a ribosome binding site.

All of the catalysts of this invention are characterized at their active site by two parallel cofacial π-conjugated quasi-planar ring systems, each of the ring systems chelating a metal ligand that catalyzes the desired reaction.

The only requirement for the π-conjugated quasi-planar ring systems of this invention is that they be capable of chelating a metal ligand. However, it is preferable to use chelating ring systems that occur naturally in biological systems. The tetrapyrrole derivatives such as the porphyrins and protoporphyrins that comprise naturally occurring hemes, pigments and cytochromes are suitable candidates for this system.

Porphyrins unsubstituted in the meso-positions are found to be susceptible to oxidation. Thus, in the preferred embodiments of this invention, the porphyrins are substituted at all four meso-positions to increase oxidation resistance. In the most-preferred embodiment of this invention, the meso-substitutions are phenyl groups.

The metal ligands of this invention change their oxidation state in the course of the performed catalysis. Depending on the reaction catalyzed, the metal ligand is selected so that the reduction potentials between the relevant oxidation states permit the catalysis reactions to occur. Suitable ligands for most biological reactions are iron(III), manganese(III), copper(II) and cobalt(III), but other transition metals will also be useful.

The first cage component is the bridging unit that covalently links the two ring systems of the catalyst. Although as few as two bridging units may be employed, the presence of additional bridging units provides more stability and rigidity to the catalyst. In a preferred embodiment of this invention, the ring systems are covalently linked by four bridging units. This permits the ring systems to remain nearly parallel at a predetermined and fixed distance.

The bridging units may vary in chain size, from two to ten atoms in length, more preferably from two to five atoms in length. Preferably, all bridging units in one catalyst are of the same length. However, bridging units varying in length could be used to provide asymmetrical catalytic sites. Also, preferably, the chains are not easily susceptible to cleavage, and therefore do not contain ester or amide linkages. In a preferred embodiment of this invention, the bridging units are straight chain alkylene bridges, —$(CH_2)_n$—, or straight chain alkylene bridges with an interposed ether linkage or amine linkage.

The bridging units may be covalently linked to the ring systems at any point on those systems. Where the ring systems are porphyrin derivatives, the bridging units may be attached directly to the rings at the pyrrole sites or at the meso-positions. In a preferred embodiment of this invention, the bridging units are attached to the porphyrin rings through their meso-substituents. Where the meso-substitutions are phenyl rings, for example, the bridging units are attached to the phenyl rings.

The second cage component comprises the two capping groups that cover the extrafacial planes of the ring systems with an inert matrix to prevent cellular or sinovial fluid constituents from approaching the metallo-ring system moieties. Any unreactive group that covers the metallo-ring system to bar biomolecular access will function as a proper capping group. The capping groups are covalently linked to the ring systems of the catalyst. The covalent linkage may be directly to the ring system, either a ring atom or a ring substituent, or indirectly through the bridging units.

In a preferred embodiment of this invention, the capping groups are aryl, cycloalkyl or aromatic heterocycles that are attached to the ring systems through one or more alkylene bridges. In the most preferred embodiment of this invention, the capping groups are phenyl groups linked to the porphyrin ring systems through four pentylene bridges that attach to meso-substituted phenyl groups on the porphyrin rings.

Optionally, the catalysts of this invention include the third cage component, the concentrating groups. The concentrating groups are small, charged moieties with a charge opposite to that of the reactants for the catalyst. The concentrating groups are covalently attached to the bridging units. If the bridging units contain an amine linkage, the concentrating groups are preferably attached through the amine nitrogen. Positively charged concentrating groups include ammonium, alkylammonium, diazonium, guanido, or histidine. Negatively charged concentrating groups include carboxylates, sulfates, sulfites, nitrates, nitrites, phosphates, phosphonates, phosphites, arsenates and the like.

Synthesis:

FIG. 1 displays an overall synthesis for a catalyst of this invention.

It will be seen by one skilled in the art that the materials and procedures of this synthesis may be varied to obtain a broad range of catalysts.

The size of the bridging units may be varied by altering the 5-substituent of the starting indene in FIG. 1. The methyl carbon of the starting compound (5-methoxyindene) is destined to become a bridging unit carbon. Longer bridges could be obtained using alterations of this substituent.

The number of bridging units is controlled by the reactant in step G in FIG. 1. The use of a tetraformylbenzene results in four bridging units. It will be seen that a triformylbenzene could be used to obtain a catalyst with three bridging units instead. Step G also dictates the nature of the capping group and the number of covalent linkages between the capping group and the ring system. The central capping group could be altered by using a tetraformylnaphthalene, or a tetraformylcycloaliphatic system, instead of a tetraformylbenzene. Here again, the number of formyl groups dictates the number of covalent linkages.

The concentrating groups are optionally added at steps N and O. These steps may be changed to obtain different protecting groups. For example, an alkylammonium chloride may be substituted for ammonium chloride in step O to obtain an positively charged alkylguanido concentrating group.

The metal ligands are added at step M. The substitution of $CuBr_2$ for $FeBr_2$, for example, will result in copper(II) ligands instead of iron.

Finally, it will be seen that the porphyrin ring system is formed in step L. The use of substituted pyrroles in this step, for example, could be used to slightly alter the nature of the ring system.

The synthesized catalyst may then be tested by common bioassays for enzymatic activity. When the catalyst is a superoxide dismutase/catalase mimic, it may be assayed for SOD enzymatic activity. An illustrative assay technique is described by Marklund and Marklund, *Eur. J. Biochem.* (1974) 47:469–474.

Pharmaceutical Compositions:

The catalysts of this invention are useful in remedying deficiencies in proteins whose catalysis they mimic. The catalysts can be administered to subjects exhibiting such conditions using standard formulations such as those set forth in *Remington's Pharmaceutical Sciences*, Mack Publishing Co., Easton Pa., (latest ed.).

Thus the present invention also provides compositions containing an effective amount of compounds of the present invention, including the nontoxic addition salts, amides and esters thereof, which may serve to provide therapeutic benefits. Such compositions can also be provided together with physiologically tolerable liquid, gel or solid diluents, adjuvants and excipients.

These compounds and compositions can be administered to mammals for veterinary use, such as with domestic animals, and clinical use in humans in a manner similar to other therapeutic agents. In general, the dosage required for therapeutic efficacy will range from about 5 to 100 $\mu g/kg$, more usually 10 to 50 $\mu g/kg$ host body weight. Alternatively, dosages within these ranges can be administered by constant infusion over an extended period of time, until the desired therapeutic benefits have been obtained.

Typically, such compositions are prepared as injectables, either as liquid solutions, emulsifications, or suspensions. Solid forms suitable for solution in, or suspension in liquid prior to injection may also be prepared. The active ingredient is often mixed with diluents or excipients which are physiologically tolerable and compatible with the active ingredient. Suitable diluents and excipients are, for example, water, saline, dextrose, glycerol, combinations thereof and the like. In addition, if desired, the compositions may contain minor amounts of auxiliary substances such as wetting or emulsifying agents, stabilizing or pH-buffering agents and the like.

The compounds may also be administered in controlled- or sustained-release formulations. These formulations are made by incorporating the catalyst in carriers or vehicles such as liposomes, nonresorbable impermeable polymers such as ethylene-vinyl acetate copolymers and Hytrel ® copolymers, swellable polymers such as hydrogels, or resorbable polymers such as collagen to provide for sustained release over an extended time period, typically from one day to one week. Liposomes used for controlled-release formulations may contain molecules used to target the liposomes to specific cells or receptors.

The compositions are conventionally administered parenterally, by injection, for example, either subcutaneously or intravenously. Additional formulations which are suitable for other modes of administration include suppositories, intranasal aerosols, and in some cases, oral formulations. For suppositories, traditional binders and excipients may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained-release formulations, or powders, and contain 10%–95% of active ingredient, preferably 25%–70%.

Other Uses:

The catalysts of this invention may be used in cosmetic applications, such as to protect skin and maintain the integrity of the natural keratinic structure of skin and hair. The compositions for dermal application containing the catalysts of this invention may be solution-type lotions; milk-type emulsions having a liquid or semi-liquid consistency; a cream or gel-type suspension or emulsion; a solid preparation such as a soap or cleansing bar; or fluids packaged under pressure in an aerosol container together with an aerosol propellant.

The cosmetic compositions for the skin may contain, in addition to a catalyst of this invention, active components or excipients conventionally employed in the formulations, such as surface active agents, dyes, perfumes, preservatives, emulsifying agents, liquid vehicles such as water, fatty bodies such as natural or synthetic oils destined to constitute the fatty phase of milks or creams, resins, fatty alcohols such as cetyl alcohol, polyoxyethylenated fatty alcohols or waxes.

Compositions for application to hair may be provided in aqueous, alcoholic, or hydroalcoholic solutions, or in the form of creams, gels, emulsions or aerosols. Such compositions may contain, in addition to a catalyst of this invention, various conventional adjuvants such as perfumes, dyes, preservatives, sequestering agents, thickening agents and the like. These compositions may be shampoos, hair setting lotions, hair treating lotions, hair styling creams or gels, hair dyes, colorants and the like.

Cosmetic compositions of the present invention generally include 0.01 to 5 percent by weight, more preferably 0.05 to 1 percent by weight synthetic catalyst.

The catalysts of this invention may also be used as part of a composition acting as a preservative and antioxidant for foodstuffs. Such compositions may contain, in addition to a catalyst of this invention, common excipients and adjuvants, other lipids and antioxidants such as pyrogallol and ascorbic acid. These compositions generally include 0.01 to 5 percent by weight, more preferably 0.05 to 1 percent by weight synthetic catalyst.

The following examples are intended to illustrate the invention but not to limit its scope.

EXAMPLE 1

Synthesis of Uncapped Cofacial-bisporphyrins With Four Three-Atom Length Bridging Units

A. Materials $R_f$s were obtained on E.M. Sciences 0.2-mm-thick precoated, plastic-backed silica gel 60 F-254 plates. $^1$H NMR spectra of CDCl$_3$ or (CD$_3$)$_2$SO solutions (Me$_4$Si as internal standard) were measured on Nicolet NT-300 and General Electric GN-500 spectrophotometers and $^{13}$C NMR spectra of CDCl$_3$ solutions on the latter instrument, operating at 125.7 MHz in the Fourier transform mode. The carbon shifts are in parts per million downfield from Me$_4$Si. Infrared spectra of chloroform solutions were recorded on a Perkin-Elmer 1330 spectrophotometer. UV/vis spectra of chloroform solutions were obtained on Perkin-Elmer 553 Fast Scan and Cary 14 spectrophotometers. Fast atom bombardment mass spectroscopy (FABMS) was performed at UCSB by Dr. Hugh Webb using m-nitrobenzylalcohol as the matrix and a parallel run of cesium rubidium iodide for the reference. Laser desorption mass spectroscopy was performed in the laboratory of Professor Charles Wilkins at UCR. Elemental analyses were performed at Galbraith Laboratories, Inc. All reactions were carried out with purified reagents in dry, purified solvents under an atmosphere of argon or nitrogen unless noted otherwise. Chromatographic separations were obtained with Fischer type 60A (200–425 mesh) silica gel, Aldrich aluminum oxide (150 mesh, converted to Brockmann III activity level). Preparative thin-layer chromatography (TLC) was performed using E.M. Sciences Kieselgel 60 F$_{254}$ and aluminum oxide 60 F$_{254}$ (Type E) glass-backed plates.

Figure 2:
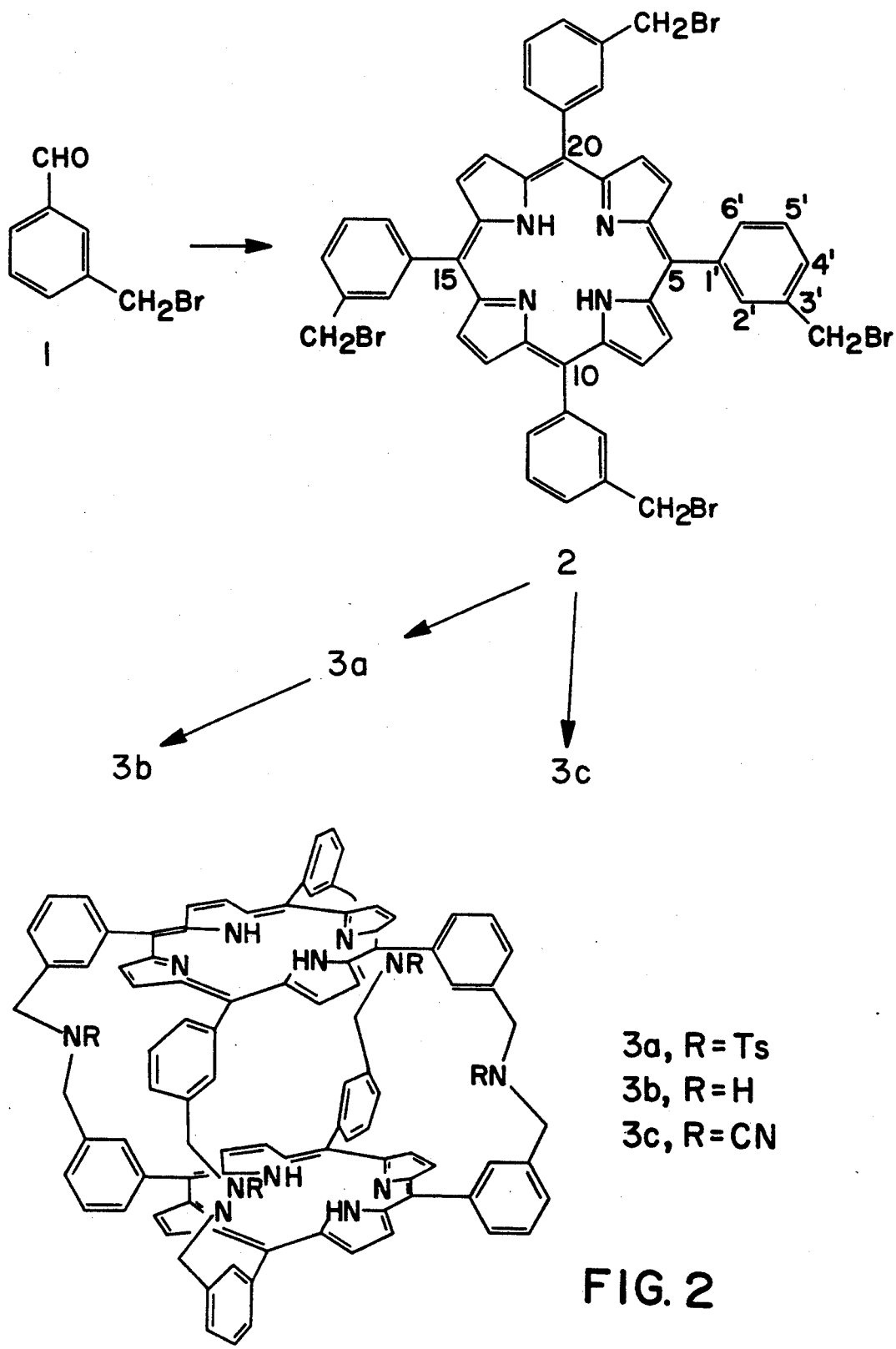
FIG. 2 details schemes for the synthesis of cofacial-bisporphyrins with four two- or three-atom bridges.
Figure 2A:
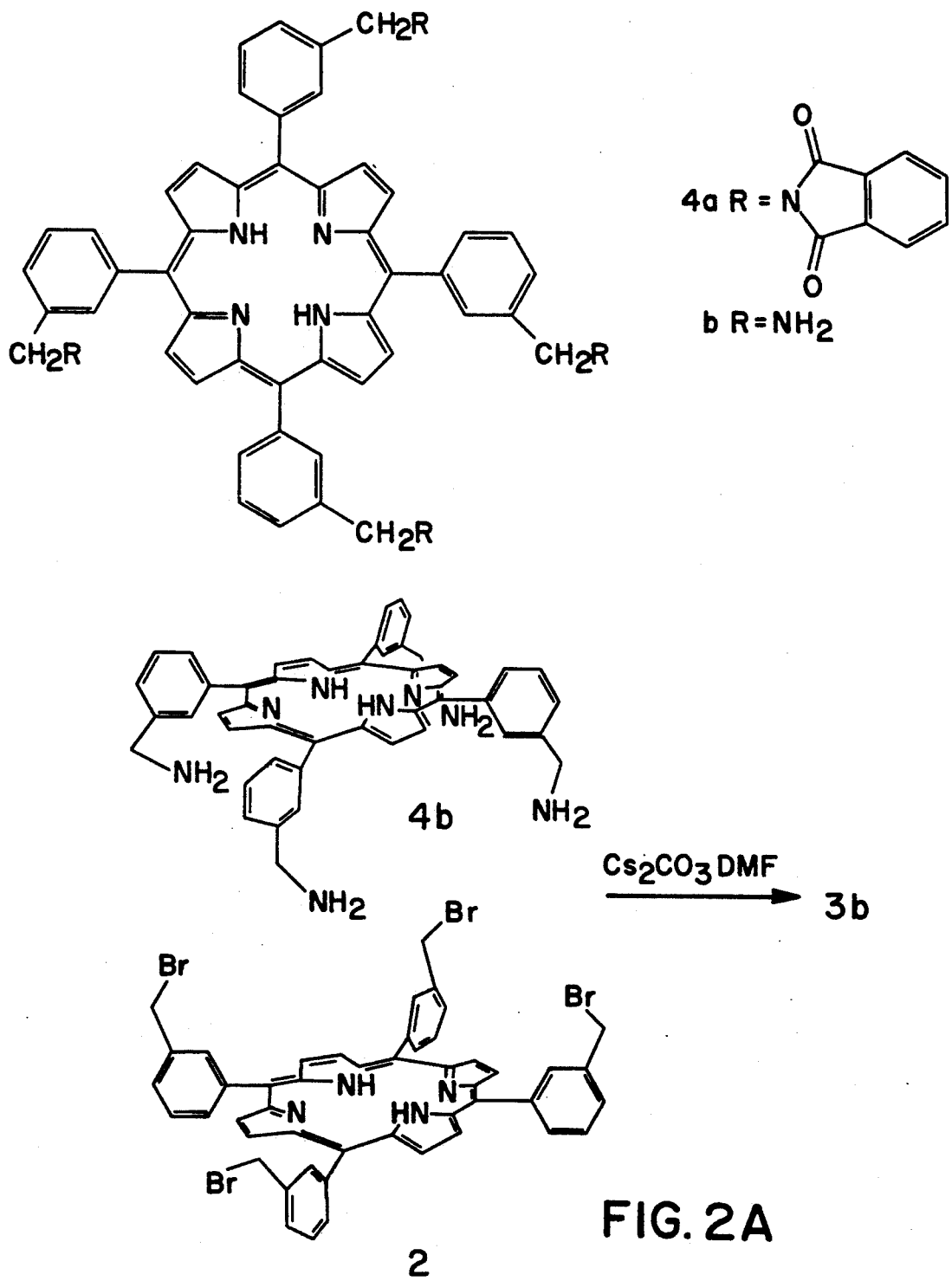
Figure 2B:
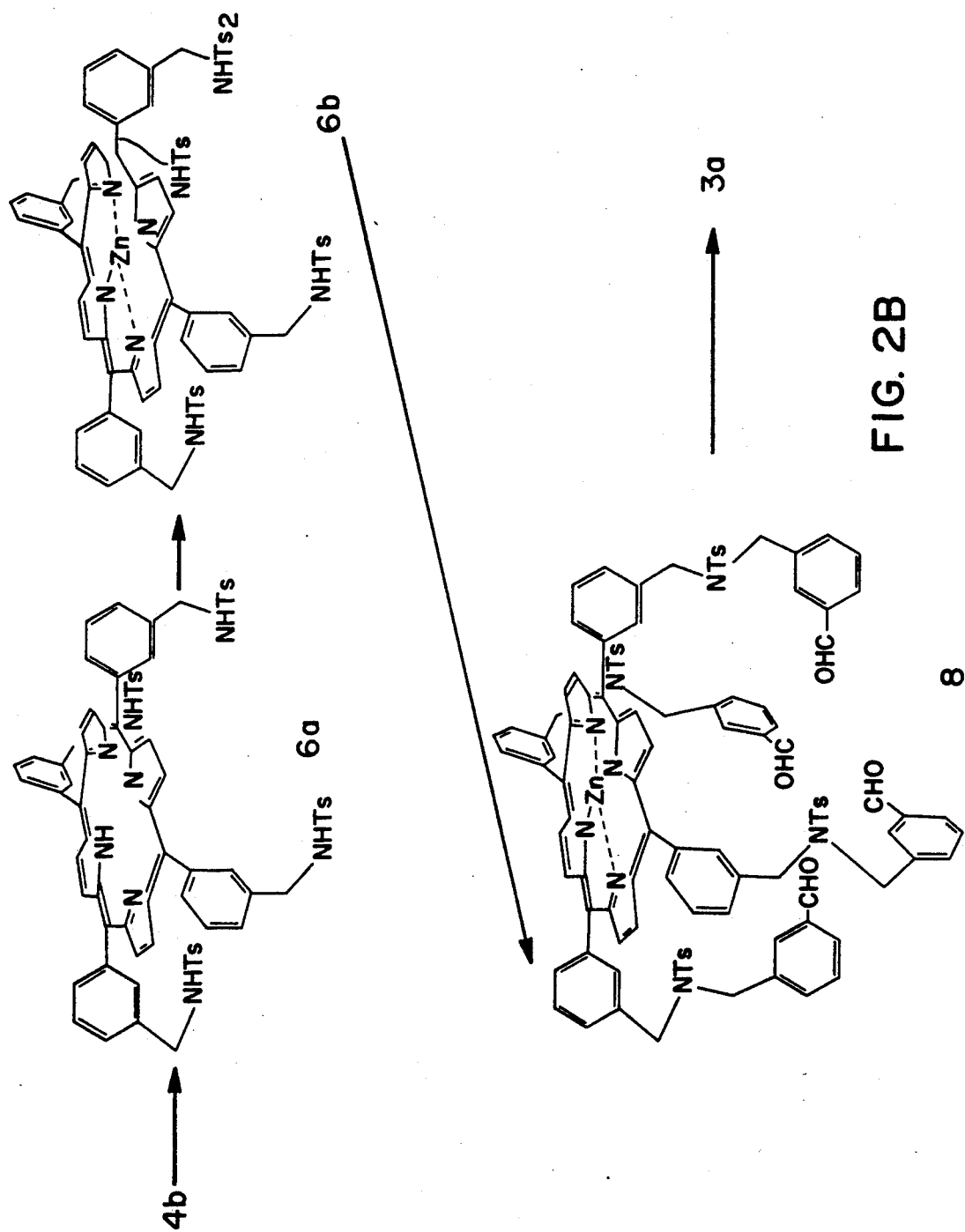
Figure 2C:
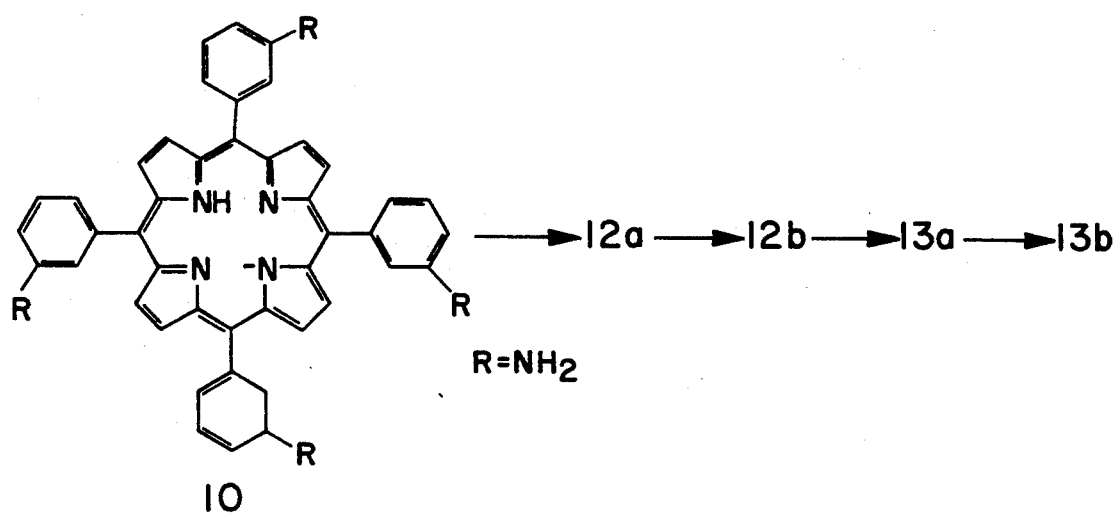
Figure 2C:
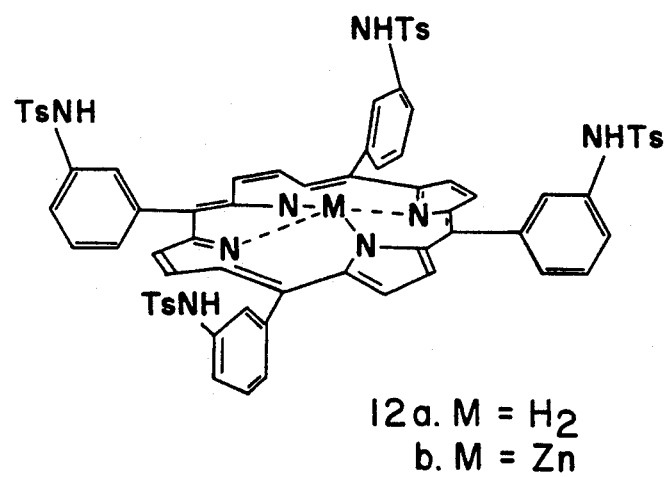
Figure 2C:
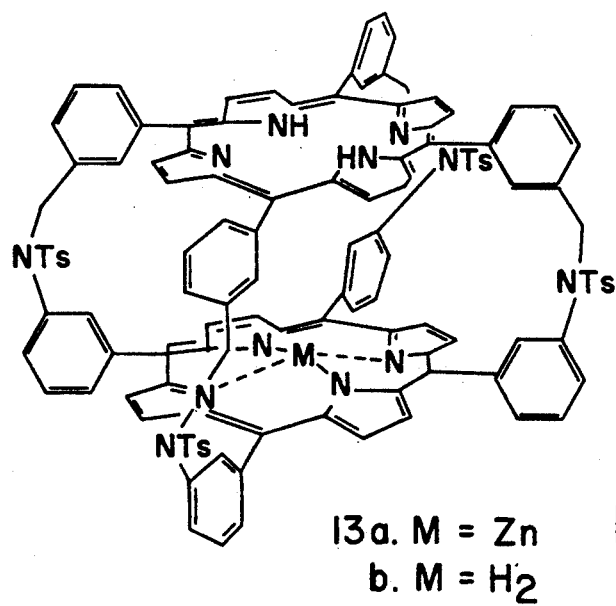

Synthesis of the following numbered compounds refer to the synthetic steps outlined in FIG. 2.

B. Synthesis of α-Bromo-m-tolualdehyde (1).

A solution of diisobutylaluminum hydride (92 ml, 1M in hexanes, 92 mmol) was added dropwise via syringe pump injector over a period of 45 min to a solution of α-bromo-m-tolunitrile (15.000 g, 76.5 mmol) in 155 ml of chlorobenzene at 0° C. The resulting mixture was stirred at 0° C. for 1 h, then 100 ml of 10% aqueous HCl was added and stirring continued at 0° C. for 10 min. The layers were separated and the aqueous layer extracted with ether (2×). The organic solutions were combined and washed vigorously with 10% HCl for 10 min, then water (2×) and brine, dried over MgSO$_4$ and evaporated to give a crystalline solid which was then dissolved in a minimal amount of ether (10–15 ml) and layered with petroleum ether (30–40 ml). The resulting spiny white crystals were collected and washed with ice-cold petroleum ether to yield 10.791 g (71%) of aldehyde 1: m.p. 46°–49° C.; $^1$H NMR δ 4.54 (s, 1, CH$_2$Br), 7.52 (t, 1, J=8 Hz, H-5), 7.67 (br d, 1, J=8 Hz, H-4), 7.82 (dt, 1, J=8, 1 HZ, H-6), 7.90 (br s, 1, H-2), 10.02 (s, 1, CHO); $^{13}$C NMR δ 32.0 (CH$_2$Br), 129.6, 129.7 and 129.8 (C-2, C-5 and C-6), 134.8 (C-4), 136.8 (C-1), 138.9 (C-3), 191.6 (CHO); IR υ 1595 and 1610 (m, C=C), 1710 (s, C=O), 2740 and 2820 (m, CHO) cm$^{-1}$.

Anal. Calcd for C$_8$H$_7$OBr: C, 48.27; H, 3.54. Found: C, 48.05; H, 3.48.

C. Synthesis of 5,10,15,20-Tetrakis-(α-bromo-m-tolyl)-porophyrin (2) ("m-CH$_2$BrTPPH$_2$")

A solution of boron trifluoride etherate (0.81 ml, 6.6 mmol) was added to a mixture of aldehyde 1 (3.979 g, 20 mmol) and pyrrole (1.39 ml, 20 mmol) in 2 l of dry CHCl$_3$ and the resulting solution stirred at room temperature for 1 h. Triethylamine (0.93 ml, 6.6 mmol) and then tetrachloro-1,4-benzoquinone (3.688 g, 15 mmol) were added and the mixture refluxed for 1 h. The solvent was evaporated down to about 100 ml, the solution filtered and the green-black precipitate washed with CHCl$_3$. The filtrate was evaporated, the residue extracted with ether, the resulting ether solution filtered and the insoluble solid washed with ether until it was only pale-red. The ether filtrate was evaporated to give 988 mg (20%) of m-CH$_2$BrTPPH$_2$ (2) as purple crystals: $^1$H NMR δ −2.81 (s, 2, NH), 4.77 (s, 8, CH$_2$Br), 7.73 (t, 4, J=8 Hz, H-5'), 7.81 (d, 4, J=8 Hz, H-6'), 8.15 (d, 4, J=8 Hz, H-4'), 8.25 (s, 4, H-2'), 8.86 (s, 8, β-pyrrolic H); $^{13}$C NMR δ 33.5 (t, CH$_2$Br), 119.5 (s, meso-C), 127.2 (d), 128.4 (d), 131.3 (br s), 143.5 (d), 135.0 (d), 136.4 (s, C-3'), 142.5 (s, C-1'); IR υ 3330 (w, N-H), 1610, 1590 and 1565 (m, C=C) cm$^{-1}$; UV/vis λ$_{max}$(ε×10$^{-3}$), 419.5 (324), 515 (16.1), 549 (7.21), 589 (5.50), 646 (3.42) nm; FABMS calcd for C$_{48}$B$_{34}$Br$_4$N$_4$ (M+) m/e 982, found m/e 982.

Anal. Calc'd for C$_{48}$H$_{34}$Br$_4$N$_4$: C, 58.45; H, 3.47; N, 5.68. Found: C, 58.03; H, 3.42; N, 5.57.

D. Synthesis of Tetra-[m,m'-(methylene-N-(p-toluenesulfonamido)-methylene)]-strati-bis-5,10,15,20-tetrakisphenylporphyrin (3a) ("TsN-(m-CH$_2$TPPH$_2$)$_2$")

A mixture of m-CH$_2$BrTPPH$_2$ (2) (237 mg, 0.24 mmol), p-toluenesulfonamide (82 mg, 0.48 mmol) and cesium carbonate (469 mg, 1.44 mmol) in 240 ml of dimethylformamide was stirred at room temperature for 14 h, then diluted with 100 ml of CHCl$_3$. This solution was washed with water (3×300 ml) and the organic layer separated, dried over Na$_2$SO$_4$ and evaporated. The purple residue was further dried at 110° C. (0.2 mm Hg) to give 192 mg purple solid. This was subjected to flash-chromatography through a short column (4×0.75 in) of silica, eluting with CHCl$_3$ to give 125 mg of purple solid. This was divided into two fractions and each fraction was subjected to preparative TLC on a 0.5×200×200 mm silica plate, eluting with CHCl$_3$ (developed twice). The major purple band and trailing green-brown band were collected and the residue obtained stirred in a solution of trifluoroacetic acid (0.5 ml) for 20 min. This green solution was diluted with CHCl$_3$ and washed with a 5% NH$_4$OH solution, water and then brine, dried over Na$_2$SO$_4$, and evaporated to give 18 mg (7.5%) of TsN-(m-CH$_2$TPPH$_2$)$_2$ (3a) as a purple solid: $R_f$ 0.42 (100:1, CHCl$_3$:methanol); $^1$H NMR δ −4.42 (s, 4, NH), 2.51 (s, 12, tosyl CH$_3$), 4.66 (s, 16, benzylic CH$_2$), 7.14 (s, 8, H-2'), 7.58 (t, 8, J=8 Hz, H-5'), 7.75 (d, 8, J=8 Hz, H-4'), 7.89 (d, 8, J=8 Hz, H-6'), 8.17 (s, 16, β-pyrrolic H); $^{13}$C NMR δ 21.6 (tosyl CH$_3$), 49.3 (benzylic CH$_2$), 118.4 (meso-C), 127.2 (d, J=160 Hz), 127.6 (d, J=161 Hz), 128.7 (d, J=156 Hz), 129.8 (d, J=160 Hz), 133.2 (d, J=160 Hz), 133.4 (tosyl p-C), 135.1 (d, J=156 Hz), 138.4 (C-3'), 141.7 (C-1'), 143.6 (tosyl ipso-C), 153.1 (br s); IR Σ 3322 (W, N-H), 1601 (m, C=C), 1156 and 1090 (s, SO$_2$) cm$^{-1}$; UV/Vis $\lambda_{max}(\epsilon \times 10^{-3})$ 408 (sh, 368), 415 (470), 516 (49.2), 551 (21.5), 592 (16.0), 648 (5.21) nm; FABMS calc'd for C$_{124}$H$_{96}$N$_{12}$O$_8$S$_4$ (M+) m/e 2008.6, found 2008.0; laser desorption MS calc'd for $^{12}$C$_{123}$$^{13}$C$_1$H$_{96}$N$_{12}$O$_8$S$_4$ (M+) m/e 2009.63905, found m/e 2009.67262.

E. Synthesis of Tetra-[m,m'-(methylene-aza-methylene)]strati-bis-5,10,15,20-tetrakisphenylporphyrin (3b) (HN-("m-CH$_2$TPPH$_2$)$_2$") via reduction of (3a).

To a solution of TsN(m-CH$_2$TPPH$_2$)$_2$ (3a) in 0.5 ml of dry dimethoxyethane at −60° C. was added a solution of sodium biphenyl radical anion in dimethoxyethane. (The anion was prepared by mixing biphenyl (382 mg, 2.5 mmol) with sodium metal (57 mg, 2.5 mmol) in 20 ml dimethoxyethane overnight at room temperature and found to be 0.028M immediately prior to this reaction by titration against N,N-methylphenyl-p-toluenesulfonamide.) After an initial 0.8 ml addition of biphenyl radical anion solution, the progress of the reaction was monitored by TLC at intervals after every 0.2 ml addition of the solution. The reaction was quenched with wet ether when TLC analysis (100:1, CHCl$_3$:methanol) showed no (or very little) fast running 3a remaining, with the product staying at the baseline (1.7 ml total biphenyl radical anion solution). The solution was diluted with CHCl$_3$ and then washed with water and brine, dried over Na$_2$SO$_4$ and evaporated to give a residue which was dissolved in a minimal amount of CHCl$_3$ and then caused to precipitate by addition of hexanes. The precipitate was collected on a small (0.5×1 cm) bed of celite in a pipette and rinsed with hexanes. The precipitate was then washed off of the celite with CHCl$_3$ and the filtrate evaporated to give 2.3 mg (41%) of HN(m-CH$_2$TPPH$_2$)$_2$ (3b) as a purple solid: $^1$H NMR δ −3.78, −3.68, −2.8 (br) (all s, 4, pyrrolic NH), 3.8 (br s), 4.19 (sh), 4.21 (all s, 16, benzylic CH$_2$), 7.56–7.60 (m, 16, H-4' and H-5'), 7.81 (s, 8, H-2'), 7.95 (br d, 8, J=7 Hz, H-6'), 8.43, 8.46 (sh), 8.8 (br) (all s, 16, β-pyrrolic H); IR υ 3320 (w, N-H), 1600 (m, C=C) cm$^{-1}$; UV/vis $\lambda_{max}(\epsilon \times 10^{-3})$ 406 (sh, 137), 414 (258), 515 (15.9), 550 (9.51), 590 (7.78), 646 (5.85) nm; laser desorption MS calc'd for $^{12}$C$_{95}$$^{13}$C$_1$H$_{72}$N$_{12}$ (M−) m/z 1393.6036, found m/z 1393.7149.

F. Synthesis of Tetra-[m,m'-(methylene-N-(cyanamido)-methylene)]-strati-bis-5,10,15,20-tetrakisphenylporphyrin (3c) ("NCN-(m-CH$_2$TPPH$_2$)$_2$")

Compound 3c was prepared in exactly the same manner as 3a using m-CH$_2$BrTPPH$_2$ (228 mg, 0.23 mmol), cyanamide (19.4 mg, 0.46 mmol), cesium carbonate (450 mg, 1.38 mmol) and dimethylformamide (230 ml). The initial crude residue (144 mg after drying) weighed 58 mg after short column chromatography and this was subjected to preparative TLC on a 0.5×200×200 mm silica plate, eluting with 150:1 (CHCl$_3$:methanol) and the second most nonpolar purple band was isolated to give 13 mg (7.6%) of NCN-(m-CH$_2$TPPH$_2$)$_2$ (3c) as a purple solid: $R_f$ 0.20 (100:1, CHCl$_3$:methanol); $^1$H NMR δ −3.99 (s, 4, NH), 4.43 (s, 16, benzylic CH$_2$), 7.31 (s, 8, H-2'), 7.74 (t, 8, J=8 Hz, H-5'), 7.84 (d, 8, J=8 Hz, H-4'), 8.13 (d, 8, J=8 Hz, H-6'), 8.38 (s, 16, β-pyrrolic H); IR υ 3320 (w, N-H), 2230 (s, C≡N) 1600 and 1580 (m, C=C) cm$^{-1}$; UV/vis $\lambda_{max}(\epsilon \times 10^{-3})$ 415 (454), 514 (20.5), 550 (9.87), 591 (6.40), 645 (3.47) nm; FABMS calc'd for C$_{100}$H$_{68}$N$_{16}$ (M+) m/e 1492.6, found m/e 1492.4.

EXAMPLE 2

Alternate Synthesis for Cofacial-Bisporphyrin 3b

A. Synthesis of 5,10,15,20-Tetrakis-(α-N-phthalimido-m-tolyl) porphyrin (4a)

A mixture of m-CH$_2$BrTPP (2) (470 mg, 0.476 mmol) and potassium phthalimide (882 mg, 4.76 mmol) in 8 ml of dimethylformamide was stirred for 14 h at room temperature, then diluted with water and the resulting precipitate collected and dried at 110° C. for 4 h to give 566 mg (95%) of tetraphthalimide 4a as a purple solid greater than 90% pure by $^1$H NMR: $^1$H NMR δ −2.90 (s, 2, NH), 5.14 (m, 8, benzylic CH$_2$), 7.68 (m, 16, phthalimide Hs), 7.83 (m, 8, H-5' and H-6'), 8.10 (m, 4, H-4'), 8.28 (m, 4, H-2'), 8.79 and 8.81 (s, 8, β-pyrrolic H); IR υ 320 (w, N-H), 1765 (w, C=O), 1715 (s, C=O), 1600 (m, C=C) cm$^{-1}$; UV/vis $\lambda_{max}(\epsilon \times 10^{-3})$ 420 (304), 516 (15.8), 550 (6.76), 590 (4.79), 646 (3.24) nm; FABMS calc'd for C$_{80}$H$_{50}$N$_8$O$_8$ (M+) m/e 1250, found m/e 1250.

B. Synthesis of 5,10,15,20-Tetrakis-(α-amino-m-tolyl) porphyrin (4b) ("m-CH$_2$NH$_2$TPPH$_2$")

A mixture of the tetraphthalimide 4a (534 mg, 0.427 mmol), benzyltriethylammonium chloride (97 mg, 0.427 mmol), 85% hydrazine (5 ml) and 43 ml of CHCl$_3$ was stirred for 14 h at room temperature, then diluted with CHCl$_3$ and washed with 5% NaOH, H$_2$O and brine, dried over Na$_2$SO$_4$ and evaporated. The purple solid obtained was dried at 110° C. (0.2 mm Hg) for 3 h to give 232 mg (74%) of 4b as a purple solid: $^1$H NMR δ −2.78 (s, 2, pyrrolic NH), 1.80 (br s, 8, amino NH$_2$), 4.16 (s, 8, benzylic CH$_2$), 7.71 (br s, 8, H-5' and 6'), 8.14 (br s, 8, H-2' and H-4'), 8.84 (s, 8, β-pyrrolic H); IR υ 3300 (w, N-H), 1590 and 1570 (m, C=C) cm$^{-1}$; UV/vis $\lambda_{max}(\epsilon \times 10^{-3})$ 419.5 (178), 516 (9.71) 554 (4.85), 591 (3.64), 648 (3.81) nm; FABMS calc'd for C$_{48}$H$_{42}$N$_8$ (M+) m/e 730, found m/e 730.

C. Synthesis of Tetra-[m,m'-(methylene-aza-methylene)]-strati-bis-5,10,15,20-tetrakisphenylporphyrin (3b) ("HN-(m-CH$_2$TPPH$_2$)$_2$") via reaction of tetrabromide 2 with tetraamine 4b A solution of m-CH$_2$BrTPPH$_2$ (2) (60 mg, 0.061 mmol), m-CH$_2$NH$_2$TPPH$_2$ (4b) (44 mg, 0.061 mmol) and Cesium carbonate (159 mg, 0.49 mmol) in 60 ml of dimethylformamide was stirred at room temperature for 14 h, then diluted with 60 ml of CHCl$_3$. The resulting solution was washed with water and brine, dried over Na$_2$SO$_4$ and evaporated (with the residual DMF being removed on a rotary evaporator at about 50° C. (3 mm Hg)). The residue was dissolved in CHCl$_3$ and filtered. The filtrate was concentrated and then subjected to preparative TLC on a 0.25×200×200 mm alumina plate eluting with 100:20:1 (CHCl$_3$:Hexanes:methanol). The baseline band was collected to give 1 mg (2.4%) of HN-(m-CH$_2$TPPH$_2$)$_2$ (3b) as a purple solid which had a 500 MHz H NMR identical to that obtained from reduction of TsN-(m-CH$_2$TPPH$_2$)$_2$ (3a) with sodium biphenyl radical anion (see above).

EXAMPLE 3

Alternate Synthesis of Cofacial-Bisporphyrin 3a

A. Synthesis of 5,10,15,20-Tetrakis-(α-N-(p-toluenesulfonamido)-m-tolyl)-porphyrin (6a) ("m-CH$_2$NH(Ts)TPPH$_2$")

A mixture of m-CH$_2$NH$_2$TPPH$_2$ (4b) (70 mg, 0.096 mmol), p-toluenesulfonylchloride (183 mg, 0.96 mmol) and triethylamine (0.2 ml, 1.44 mmol) in 10 ml of purified CHCl$_3$ was stirred at room temperature for 24 h then diluted with CHCl$_3$ and washed with 5% NaOH, water and brine, then dried over Na$_2$SO$_4$ and evaporated. The residue was subjected to preparative TLC on a 1.5×200×200 mm alumina plate eluting with 50:1 (CHCl$_3$:methanol) and the two major bands were collected. The less polar band (34 mg, 24%) was identified as a penta-tosylated porphyrin. The more polar band (36 mg, 28%) was identified as m-CH$_2$NH(Ts)TPPH$_2$ (6a): R$_f$ 0.14 (50A1 CHCl$_3$:methanol on silica), $^1$H NMR δ −3.03−(−2.96) (m) and −1.64 (s) (2, pyrrolic NH), 1.85–1.99 (m, 12, tosyl Me), 4.21–4.28 (m, 8, benzylic CH$_2$), 5.45, 5.60, 5.74 (all br s, 4, tosyl NH), 6.84–6.95 (m, 8, tosyl m-H), 7.43–7.65 (m, 16, H-4', H-5' and tosyl o-H), 7.90–7.97 (m, 8, H-2' and H-6'), 8.64–8.66 (m, 8, β-pyrrolic H; UV/vis λ$_{max}$ (ε×10$^{-3}$) 419.5 (262), 516 (12.6) 551 (6.05), 589 (4.79), 644 (3.53) nm; FABMS calc'd for C$_{76}$H$_{66}$N$_8$O$_8$S$_4$ (M+) m/e 1346.4, found m/e 1346.5.

B. Synthesis of 5,10,15,20-Tetrakis-(α-N-(p-toluenesulfonamido)-m-tolyl)-porphyrin Zn(II) complex (6b) ("m-CH$_2$NH(Ts)TPPZn").

A mixture of m-CH$_2$NH(Ts)TPPH$_2$ (6a) (36 mg, 0.027 mmol) and zinc chloride (36 mg, 0.27 mmol) in 1 ml of dimethylformamide was stirred at 100° C. for 2 h, then cooled and diluted with CHCl$_3$. The resulting solution was washed with water and brine, dried over Na$_2$SO$_4$ and evaporated. The residue was separated into 2 fractions and each fraction was subjected to preparative TLC on a 200×100×0.25 mm silica plate eluting with 50:1 (CHCl$_3$:methanol) along the short axis and the bright red-pink band was collected and dried at 110° C. (0.2 mm Hg) over P$_2$O$_5$ to give 16 mg (42%) of (m-CH$_2$NH(Ts)TPPZn) (6b) as a red solid: $^1$H NMR α 2.02–2.08 (m, 12, tosyl CH$_3$), 4.13–4.27 (m, 8, benzylic CH$_2$), 5.06–5.24 (m, 4, tosyl NH), 6.96–7.04 (m, 8, m-tosyl H), 7.45–7.52 (m, o-tosyl H), 7.59 (t, 4, J=8 Hz, H-5'), 7.64 (d, 4, J=8 Hz, H-4'), 7.87 (s, 4, H-2'), 7.91–7.96 (m, 4, H-6'), 8.67–8.75 (m, 8, β-pyrrolic H); UV/vis λ$_{max}$ (ε×10$^{-3}$) 423.5 (268), 516 (6,10), 551 (13.4), 590 (5.08), 652 (6.10) nm; FABMS calc'd for C$_{76}$H$_{64}$N$_8$O$_8$S$_4$Zn (M+) m/e 1410, found m/e 1410.

C. Synthesis of 5,10,15,20-Tetrakis-[α-N-(p-toluenesulfonamido-(α-N-m-tolualdehyde))-m-tolyl]porphyrin Zn(II) complex (8) ("m-CH$_2$N(Ts)(m-CH$_2$PhCHO)TPPZn")

A mixture of tetrasulfonamide 6b (18 mg, 0.013 mmol), α-bromo-m-tolualdehyde (1) (12 mg, 0.06 mmol) and cesium carbonate (50 mg, 0.153 mmol) in 1 ml of dimethylformaldehyde was stirred at 80° C. for 2 h. Then the solution was cooled, diluted with CHCl$_3$ and washed with water and brine, dried over Na$_2$SO$_4$ and evaporated. The resulting residue was subjected to preparative TLC on a 1.0×100×100 mm silica plate and eluted with 50:1 (CHCl$_3$:methanol). The fastest running purple-pink band was collected to provide 12 mg (48%) of the tetraaldehyde 8: R$_f$ 0.32 (50:1, CHCl$_3$:methanol); $^1$H NMR δ 2.03–2.16 (m, 12, tosyl CH$_3$), 4.60–4.67 (m, 16, benzylic CH$_2$s), 7.12–7.21 (m, 8, tosyl m-H), 7.37 (t, 4, J=8 Hz, phenyl H), 7.56–7.66 (m, 24, phenyl Hs), 7.76–7.79 (m, 8, tosyl o-H), 7.86, 7.94 (all s, 4, H-2'), 8.02, 8.07, 8.11 (all d, 4, J=8 Hz, H-6'), 8.68, 8.69 (all s, 8, β-pyrrolic H), 9.67–9.71 (m, 4, CHO); IR ν 1705 s, C═O), 1600 (m, C═C) 1170, 1100 and 1080 (s, SO$_2$) CM$^{-1}$; UV/vis λ$_{max}$ (ε×10$^{-3}$) 426 (311), 516 (5.54), 556 (15.7), 595 (6.57) nm; FABMS calc'd for C$_{108}$H$_{88}$N$_8$O$_{12}$S$_4$Zn (M+) m/e 1880.5, found m/e 1881.

D. Synthesis of Tetra-[m,m'-(methylene-N-(p-toluenesulfonamido)-methylene)]-strati-bis-5,10,15,20-tetraphenylporphyrin (3a) ("TsN-(m-CH$_2$TPPH$_2$)$_2$") from tetraaldehyde 8

A mixture of tetraaldehyde 8 (predried overnight in a 5 ml round bottom flask at 110° C./0.2 mm over P$_2$O$_5$) (7 mg, 0.0037 mmol), pyrrole (1 μl, 0.0149 mmol) and boron trifluoride etherate (2 μl of a 2.5M solution in CHCl$_3$, 0.005 mmol) in 1.5 ml of CHCl$_3$ (distilled off of K$_2$CO$_3$) in the above flask, glass stoppered (secured with a plastic crimp), was heated with stirring in a 65° C. oil bath for 3.5 h during which the solution became dark green. Then the solution was cooled to room temperature and triethylamine (2 μl, 0.010 mmol) was added which caused the solution color to change to red. After 15 min of stirring at room temperature, tetrachloro-1,4-benzoquinone (2.7 mg, 0.0112 mmol) was added and the resulting mixture again heated with stirring (65° C. oil bath) for 1 h. Then the solvent was evaporated and the residue obtained subjected to preparative TLC on a 0.25×200×200 mm silica plate eluting with 50:1 (CHCl$_3$:methanol) to give two nonpolar red bands and one polar red band. The polar band was collected to give 3 mg (43%) of starting tetraaldehyde 8 (identified by $^1$H NMR). The nonpolar bands were collected and combined. They were diluted with CHCl$_3$ and this solution was washed with 10% HCl, water and brine, dried over Na$_2$SO$_4$ and evaporated to give 1.5 mg (20%, 43% corrected for recovered tetraaldehyde 8) of TsN-(m-CH$_2$TPPH$_2$)$_2$ (3a) spectrally identical (500 MHz $^1$H NMR, laser desorption MS) with that previously obtained (see supra).

EXAMPLE 4

Synthesis of an Uncapped Cofacial-bisporphyrin With Four Two-Atom Length Bridging Units

A. Synthesis of 5,10,15,20-tetrakis-m-aminophenylporphyrin (10) ("m-NH$_2$TPPH$_2$")

The preparation of porphyrin 10 was improved by the following procedure:

A mixture of m-nitrobenzaldehyde (20.0 g, 132 mmol), acetic anhydride (21.8 ml, 231 mmol) and 660 ml propionic acid was heated to 140° C. and pyrrole (9.2 ml, 132 mmol) was added to this solution in a dropwise manner. After 45 min of stirring at 140° C. the solution was allowed to cool to room temperature and then stirred for 14 h open to air. The resulting precipitate was collected by filtration and washed with water and methanol. The resulting red cake was dissolved portionwise in $CH_2Cl_2$ and filtered through a 600 ml medium glass frit funnel ⅓ filled with silica gel. After passing 1 l of $CH_2Cl_2$ through the silica pad, the filtrate was concentrated down to 150 ml and 100 ml of methanol was added. This solution was reduced to about 90 ml by rotary evaporation and the precipitate collected by filtration then stirred thoroughly with about 30 ml of $CH_2Cl_2$ and filtered again. The resulting solid was dried at 110° C. (0.2 mm Hg) for 14 h over $P_2O_5$ to give 2.89 g (11%) of 5,10,15,20-tetrakis-m-nitrophenylporphyrin ("m-$NO_2$TPPH$_2$") as a purple powder: $R_f$ 0.66 (3:1, THF:hexanes); $^1$H NMR $\delta$ −2.83 (s, 2, pyrrolic NH), 8.00 (t, 4, J=7Hz, H-5'), 8.57 (d, 4, J=7Hz, H-6'), 8.72 (d, 4, J=7Hz, H-4'), 8.82 (s, 8, $\beta$-pyrrolic H), 9.09 (s, 4, H-2').

The porphyrin m-$NO_2$TPPH$_2$ (2.72 g, 3.42 mmol) was dissolved in 137 ml of concentrated aqueous HCl solution at 70°–80° C. and stannous chloride dihydrate (12.3 g, 54.8 mmol) was added. This mixture was stirred at this temperature for 30 min then cooled and 140 ml of concentrated aqueous $NH_4OH$ added carefully. To this mixture, 50 ml of $CH_2Cl_2$ was added and after thorough mixing the resulting precipitate was collected by filtration. The dark solid filter cake was crushed to a powder and mixed with THF. The resulting THF extraction and filtration sequence was repeated until the filtrate was only lightly colored. The filtrate was reduced in volume to 30 ml, 50 ml of $CHCl_3$ was added and the solution again reduced to 30 ml when another 50 ml of $CHCl_3$ was added. After reducing the solution to a final 20 ml, the precipitate was filtered and washed with $CHCl_3$ to give 2.00 g (87%) of m-$NH_2$TPPH$_2$ (10) as fine purple macrocrystals: $R_f$ 0.46 (3:1, THF:hexanes); $^1$H NMR (DMSO-d$_6$) $\delta$ −2.96 (s, 2, pyrrolic NH), 5.48 (br s, 8, NH$_2$), 7.01 (d, 4, J=7Hz, H-4'), 7.36–7.46 (m, 12, H-2', H-5' and H-6'), 8.92 (s, 8, $\beta$-pyrrolic H); FABMS calc'd for $C_{44}H_{34}N_8$ (M+) m/e 675, found m/e 675. See A. Bettelheim et al., *Inorg. Chem.* (1987) 26:1009.

B. Synthesis of 5,10,15,20-Tetrakis-m-(p-toluenesulfonamido)-phenylporphyrin (12a) ("m-(NHTs)TPPH$_2$")

A mixture of m-$NH_2$TPPH$_2$ (10) (100 mg, 0.148 mmol), p-toluenesulfonylchloride (565 mg, 2.96 mmol) and triethylamine (0.52 ml, 3.7 mmol) in 30 ml of THF was stirred at room temperature for 72 h then 10 ml of methanol was added and the solution was let stir for an additional 14 h. The mixture was then diluted with ethyl acetate, washed with water and brine, dried over $Na_2SO_4$ and evaporated. The residue was dissolved in a minimal amount of $CH_2Cl_2$ and this solution was layered with benzene. The resulting red-purple crystals were collected by filtration and dried at 110° C. (0.2 mm Hg) over $P_2O_5$ for 14 h to give 166 mg (87%) of m-(NHTs)TPPH$_2$ (12a): $R_f$ 0.62 (3:1, THF:hexanes); $^1$H NMR (DMSO-d$_6$) $\delta$ −3.17 (s, 2, pyrrolic NH), 2.34 (s, 12, tosyl CH$_3$), 7.46 (d, 8, J=7.5 Hz, tosyl m-H), 7.65 (br s, 4), 7.70–7.82 (m, 16), 7.87–7.96 (m, 4), 8.42–8.51 (m, 8, $\beta$-pyrrolic H), 10.55–10.62 (m, 4, tosyl NH); FABMS calc'd for $C_{72}H_{58}N_8O_8S_4$ (M+) m/e 1290, found m/e 1290.

C. Synthesis of 5,10,15,20-Tetrakis-m-(p-toluenesulfonamido)-phenylporphyrin Zn(II) complex (12b) ("m-(NHTs)TPPZn")

A mixture of m-(NHTs)TPPH$_2$ (12a) (100 mg, 0.077 mmol) and zinc chloride (105 mg, 0.77 mmol) in 2 ml of dimethylformamide was heated at 90° C. for 3 h, then diluted with water and brought to room temperature. The resulting precipitate was collected by filtration and dried at 110° C. (0.2 mm Hg) over $P_2O_5$ for 14 h to give 79 mg (76%) m-(NHTs)TPPZn (12b) as a red powder: $^1$H NMR (DMSO-d$_6$) $\delta$ 2.35 (s, 12, tosyl CH$_3$), 7.46 (d, 8, J=8 Hz, tosyl m-H), 7.59–7.89 (m, 24), 8.35–8.42 (m, 8, $\beta$-pyrrolic H), 10.48, 10.52 and 10.56 (all s, 4, tosyl NH); FABMS calc'd for $C_{72}H_{56}N_8O_8S_4Zn$ (M+) m/e 1352, found m/e 1350.

D. Synthesis of tetra-m,m'-(methylene-p-toluenesulfonamido)[-stratibis-5,10,15,20-tetrakisphenylporphyrin (13b) ("m,m-TsNCH$_2$-(TPPH$_2$)$_2$")

A mixture of m-(NHTs)TPPZn (12b) (34 mg, 0.025 mmol), m-CH$_2$BrTPPH$_2$ (2) (25 mg, 0.025 mmol) and cesium carbonate (33 mg, 0.10 mmol) in 50 ml of dimethylformamide was stirred at room temperature for 14 h then diluted with 75 ml of CHCl$_3$. The resulting solution was washed with water then dried ($Na_2SO_4$) and concentrated by rotary evaporation at 50° C. (0.1 mm Hg) then dried further at 110° C. (0.05 mm Hg) over $P_2O_5$ for 45 min. The residue (50 mg) was subjected to preparative TLC on a 0.5×200×200 mm silica plate eluting with 75:1 (CHCl$_3$:methanol) and the second most nonpolar violet band was isolated. It was identified as m,m'-TsNCH$_2$-(TPP)$_2$H$_2$Zn (13a): $R_f$ 0.22 (100:1, CHCl$_3$:methanol); $^1$H NMR $\delta$ −4.20 (s, 2, pyrrolic NH), 2.23 (s, 12, tosyl CH$_3$), 5.19 (s, 8, benzylic CH$_2$), 6.93 (s, 4, H-2'''), 7.48 (d, 4, J=8 Hz, H-4'' or H-4'''), 7.60 (t, 4, J=8 Hz, H-5'' or H-5'''), 7.68 (d, 4, J=8 Hz, H-4'' or H-4'''), 7.76 (t, 4, J=8 Hz, H-5'' or H-5'''), 7.79 (d, 8, J=8 Hz, tosyl o-H), 7.95 (d, 4, J=8 Hz, H-6'' or H-6'''), 8.33 (s, 8, $\beta$-pyrrolic H), 8.35 (d, 4, J=8 Hz, H-6'' or H-6'''), 8.43 (s, 8, $\beta$-pyrrolic H').

The residue m,m'-TsNCH$_2$-(TPP)$_2$H$_2$Zn (13a) was dissolved in 0.3 ml of trifluoroacetic acid and this solution was let stir for 15 min at room temperature then diluted with CHCl$_3$ and washed with 5% aqueous $NH_4OH$ solution, water and brine, dried over $Na_2SO_4$ and evaporated to give 1 mg (2.1%) of m,m'-TsNCH$_2$-(TPPH$_2$)$_2$ (13b) as a purple solid: $^1$H NMR $\delta$ −4.12 (s, 2, pyrrolic NH), −4.08 (s, 2, pyrrolic NH), 2.25 (s, 12, tosyl CH$_3$), 5.19 (s, 8, benzylic CH$_2$), 6.95 (s, 4, H-2'''), 7.50 (d, 4, J=8 Hz, H-4'' or H-4'''), 7.60 (t, 4, J=8 Hz, H-5'' or H-5'''), 7.66 (d, 4, J=8 Hz, H-4'' or H-4'''), 7.76 (t, 4, J=8 Hz, H-5'' or H-5'''), 7.79 (d, 8, J=8 Hz, tosyl o-H), 7.95 (d, 4, J=8 Hz, H-6'' or H-6'''), 8.25 (br s, 8, $\beta$-pyrrolic H), 8.35 (d, 4, J=8 Hz, H-6'' or H-6'''), 8.43 (s, 8, $\beta$-pyrrolic H'); IR $\upsilon$ 3320 (w, N-H), 1600 (m, C=C) 11270, 1170 and 1100 (s, SO$_2$) cm$^{-1}$ UV/Vis $\lambda_{max}(\epsilon \times 10^{-3})$ 415 (193), 517 (14.7), 553 (9.14), 590 (5.90), 649 (3.30) nm; FABMS calc'd for $C_{120}H_{88}N_{12}O_8S_4$ (M+) m/e 1952.6, found m/e 1953.0.

EXAMPLE 5

Synthesis of a Capped Tetrakis(pentamethylene) Porphyrin

Figure 3A:
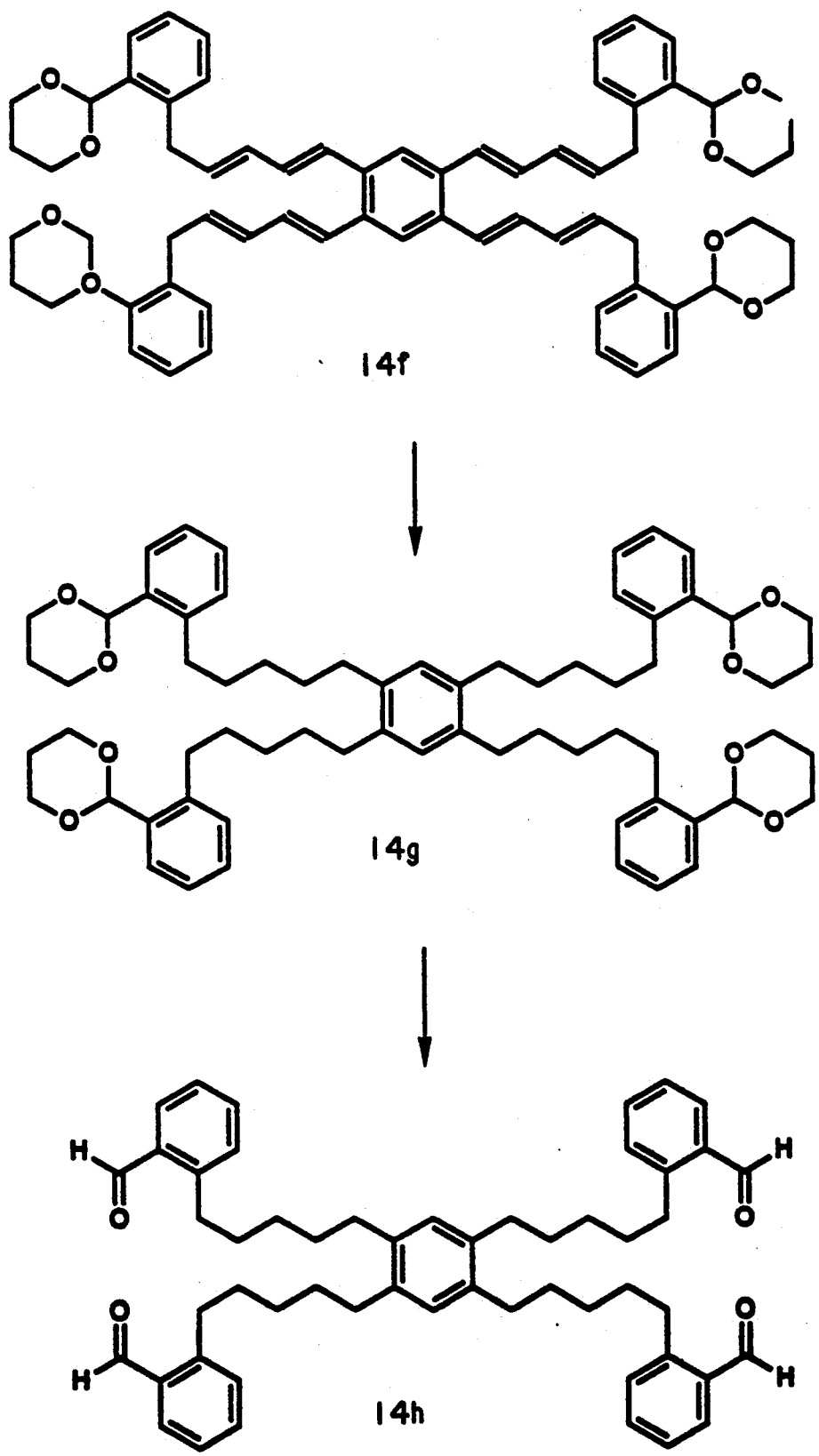
FIG. 3 outlines a scheme for the synthesis of a capped porphyrin system.
Figure 3B:
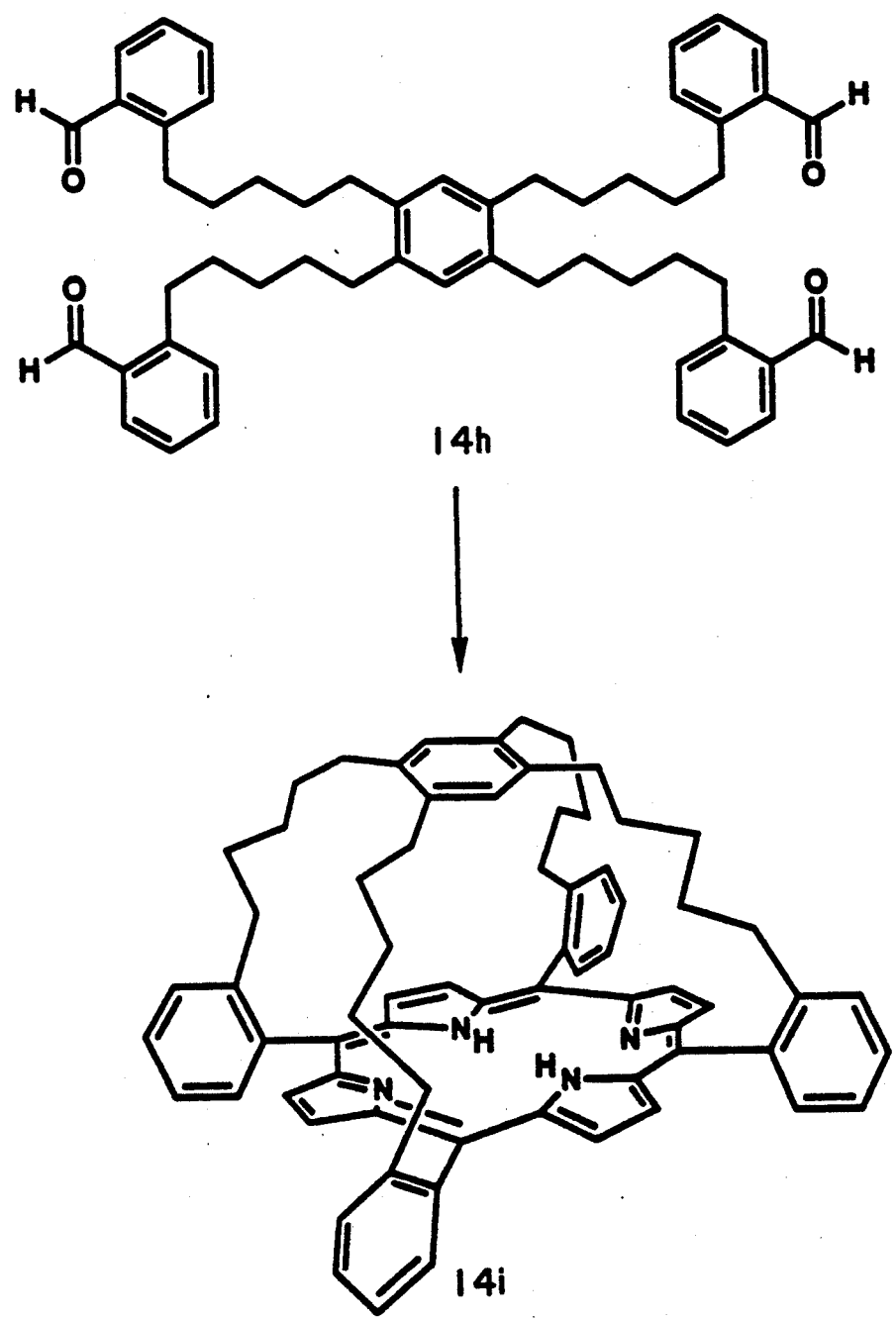
Figure 3:
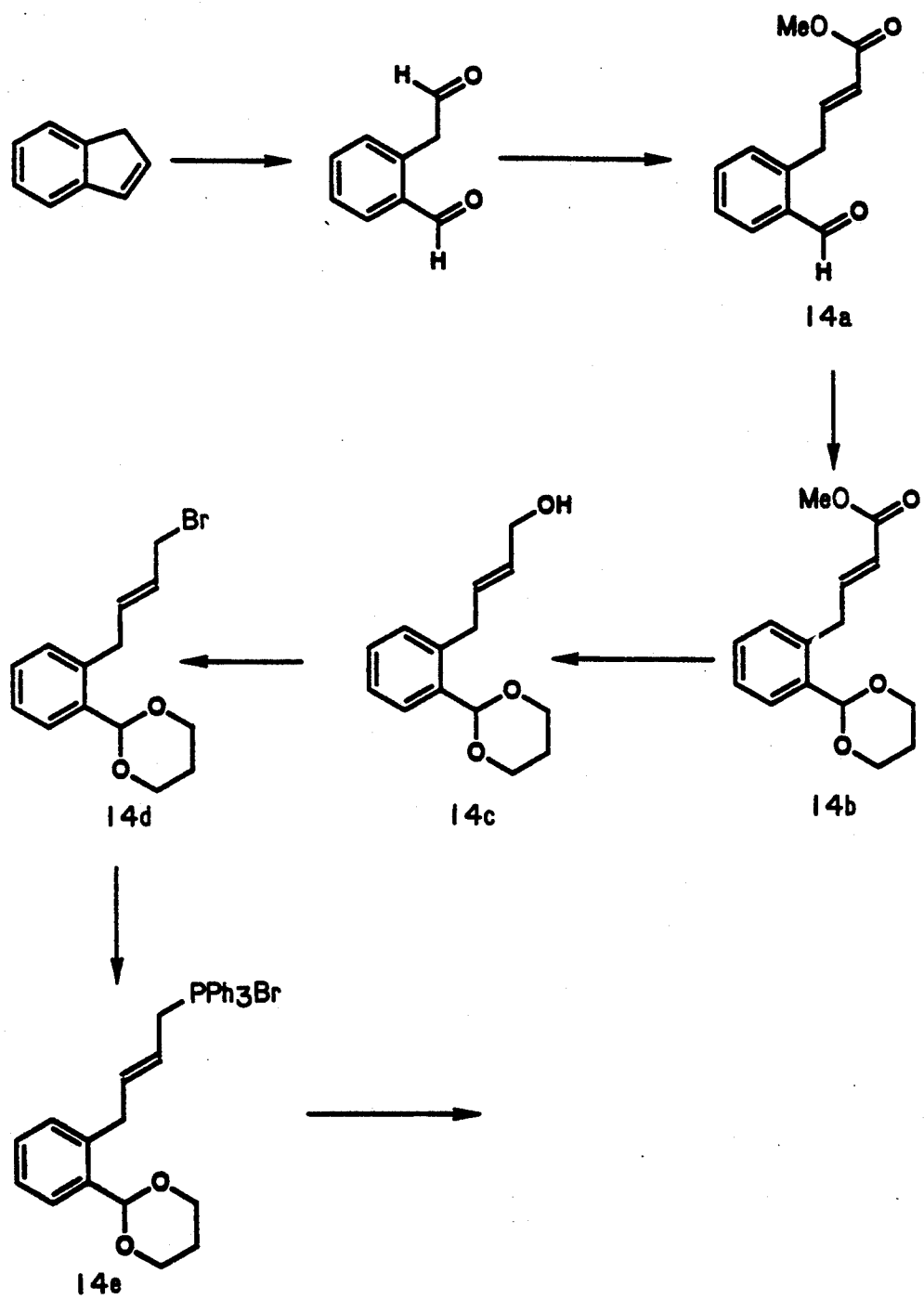

Synthesis of the following numbered compounds refer to the synthetic steps outlined in FIG. 3.

A. Preparation of 4-(2-formylphenyl)1-carboxy-2-butene, methyl ester (14a)

To a toluene (60 ml) solution of homophthalaldehyde (8.72 g; 58.9 mmol) at −80° C. was added methyl triphenylphosphoranylidene acetate (15.0 g; 45.0 mmol) in 60 ml acetonitrile:toluene (1:3). The crude mixture was adsorbed onto Florisil and chromatography on silica (10% ethyl acetate in hexanes) to provide pure 14a as a colorless oil (7.35 g; 80% yield). $^1$H NMR (CDCl$_3$, 500 MHz) δ10.07 (s, 1H, CHO), 7.77 (dd, J=6.5, 2.5 Hz, 1 H, H at C-3), 7.48 (td, J=7.5, 1.5 Hz, 1 H, H at C-4), 7.40 (ddd, J=8.0, 7.5, 1.5 Hz, 1 H, H at C-5), 7.20 (d, J=8.0 Hz, 1 H, H at C-6), 7.08 (dt, J=15.6, 6.5 Hz, 1 H, H at C-2 of butene), 5.66 (dt, J=15.6, 1.7 Hz, 1 H, H at C-3 of butene), 3.91 (dd, J=6.5, 1.7 Hz, 2 H, H's at C-1 of butene), 3.65 (s, 3 H, ester methyl), $^{13}$C NMR (CDCl$_3$, 125 MHz) δ 192.5 (CHO), 166.7 (C=O, ester), 147.1 (C-2 of butene), 139.6 (4° aromatic carbon), 134.1, 133.8, 131.4, 127.7, 122.1 (alkene and aromatic C-H's), 51.5 (ester methyl), 35.3 (C-1 of butene); IR 1720 (CHO), 1690 (ester), 1650 (C=C) cm$^{-1}$; Mass Spec. (70 ev) m/z (rel abund) 204 (M+, 2), 172 (M+-OCH$_2$, 39), 144 (M+-C$_4$H$_{10}$O$_2$H, 100), 115 (M+-C$_4$H$_{10}$O$_2$+H-C=O, 67); High Resolution Mass Spec. (HRMS) calcd for C$_{12}$H$_{12}$O$_3$: M+=204.0786. Found: 204.0759.

B. Preparation of 2-[2-(4-carboxy-3-butenyl) phenyl]-1,3-dioxane, methyl ester (14b)

To a benzene solution of 14a (7.25 g; 35.5 mmol) and propane-1,3-diol (2.69 ml; 2.84 g; 37.3 g) was added p-toluenesulfonic acid monohydrate (19.0 mg; 0.10 mmol). The solution was heated at reflux in a flask fitted with a Dean-Stark trap and condenser. Analysis of aliquots by $^1$H NMR revealed the completion of reaction within three hours. The reaction was quenched with the addition of a small amount of triethylamine. The benzene solution was then evaporated directly onto Florisil. Column chromatography (silica; 10% ethyl acetate in hexanes) provided ester 2b (9.04 g; 97%). $^1$H NMR (CDCl$_3$, 500 MHz) δ 7.56 (dd, J=7.0, 2.0 Hz, 1 H, H aromatic), 7.25 (m, 2 H, aromatic H), 7.12 (m, 2 H, aromatic and H at C-2 of butene), 5.75 (d, J=16.0, 1 H, H at C-3 of butene), 5.52 (s, 1 H, H at C-2 of dioxane), 4.22 (dd, J=11.5, 5.0 Hz, 2 H, H$^e$ at C-4 and C-6 of dioxane), 3.9 (td, J=11.5 Hz, 1.5 Hz, 2 H, H$^a$ at C-4 and C-6 of dioxane), 3.67 (s, 3 H, ester methyl), 3.66 (m, 2 H, H at C-1 of alkene), 2.18 (m, 1 H, H$^a$ at C-5 of dioxane), 1.40 (dd, J=4.0, 1.0 Hz, 1 H, H$^e$ at C-5 of dioxane); $^{13}$C NMR (CDCl$_3$, 125 MHz) δ 166.9 (C=O, ester), 148.0 (C-3 of alkene), 136.5 (4° aromatic carbon), 135.5, 130.1, 129.1, 127.0, 121.8 (alkene and aromatic C-H's), 100.4 (C-2 of dioxane), 67.5 (C-4 and C-6 of dioxane), 51.4 (ester methyl), 35.2 (C-1 of alkene), 25.7 (C-5 of dioxane); IR 2980 (aromatic (CH), 1723 (ester), 1650 (C=C-C=O) cm$^{-1}$; Mass Spec. (70 ev) m/Z (rel abund) 262 (M+, 4.5), 203 (M+-C$_3$H$_6$O, 30), 186 (M+-C$_3$H$_7$O$_2$, 67), 176 (M+-C=C-C=O(OCH$_3$), 90), 144 (M+-C$_3$H$_6$O+-COOCH$_3$, 100); HRMS calcd for C$_{15}$H$_{18}$O$_4$: M+=262.1205. Found: 262.1199.

C. Preparation of 2-[(4-hydroxy-3-butenyl)phenyl]-1,3-dioxane (14c)

To a toluene (340 ml) solution of 14b (9.04 g; 34.33 mmol) at −78° C. was added diisobutylaluminum hydride (72.1 ml of a 1M hexane solution) dropwise. After 2 h the reaction mixture was allowed to warm to 25° C. and the reaction was quenched with methanol (2 ml) and aqueous sodium potassium tartrate (100 ml of a saturated solution). The mixture was transferred to a separatory funnel and the organic layer separated. The aqueous layer was extracted with two portions of ethyl acetate (100 ml). The organic layers were combined and dried over magnesium sulfate. Column chromatography on silica (43% ethyl acetate; hexanes) provided pure 14c (6.67 g; 83% yield) $^1$H NMR (CDCl$_3$, 500 MHz) δ 7.57 (dd, J=7.5, 1.5 Hz, 1 H, H at C-5), 7.24 (m, 2 H, aromatic H), 7.13 (m, 1 H, aromatic H), 5.78 (dt, J=16.0, 7.0 Hz, 1 H, H at C-3 of butene), 5.59 (s, 1 H, H at C-2 of dioxane), 5.59 (m, 1 H, H at C-2 of butene), 4.21 (dd, J=11.0, 5.0 Hz, 2 H, H$^e$ at C-4 and C-6 of dioxane), 3.97 (m, 2 H, H at C-4 of butene), 3.92 (td, J=6.0, 2.0 Hz, 2 H, H$^a$ at C-4 and C-6 of dioxane), 3.47 (d, J=6.5 Hz, 2 H, H at C-1 of butene), 2.18 (m, 1 H, H$^a$ at C-5 dioxane), 1.39 (dd, J=14.0, 1.0 Hz, 1 H, H$^e$ at C-5 of dioxane); $^{13}$C NMR (CDCl$_3$, 125 MHz) δ 137.6, 136.3 (4° carbons of aromatic ring), 131.3, 130.3, 129.8, 129.0, 126.5, 126.4 (alkene and aromatic C-H's), 100.0 (C-2 of dioxane), 67.5 (C-4 and C-6 of dioxane), 63.2 (C-4 of alkene), 35.2 (C-1 of alkene), 25.7 (C-5 of alkene), IR 3400 (br, OH), 2980 (aromatic C—H), 2860, 1100 (C—O), cm$^{-1}$; Mass. Spec. (70 ev) m/z (rel abund) 234 (M+, 0.81), 176 (M+-C$_3$H$_5$O, 36), 158 (M+-C$_4$H$_7$O$_2$, 25), 145 (M+-hydroxybutene side chain, 28), 128 (M+-C$_4$H$_7$O$_2$+H$_2$O, 100); HRMS calcd for C$_{14}$H$_{18}$O$_3$: M+=234.1256. Found: 234.1232.

D. preparation of 2-[(4-bromo-3-butenylphenyl]-1,3-dioxane (14d)

To a solution of 14c (6.6 g; 28.2 mmol), freshly sublimed carbon tetrabromide (10.77 g; 32.5 mmol) and anhydrous collidine (4.3 ml; 3.9 g; 32.5 mmol) in dry dichloromethane (135 ml) at −20° C. was added solid triphenylphosphine (10.83 g; 41.3 ml). The reaction was complete within 30 min as demonstrated by thin-layer chromatographic analysis (silica 5% and 50% ethyl acetate in hexanes), and was quenched with the addition of methanol (2 ml) and the solvent removed. The crude mixture was chromatographed on silica (10% ethyl acetate in hexanes) to provide 14d as a colorless oil. (5.93 g; 71% yield). $^1$H NMR (CDCl$_3$, 500 MHz) δ 7.60 (dd, J=7.5, 1.5 Hz, 1 H, H at C-6), 7.25 (m, 2 H, H at C-4 and C-5), 7.12 (dd, J=7.5, 1.5 Hz, 1 H, H at C-3), 5.92 (dt, J=15.0, 6.5 Hz, 1 H, H at C-3 of butene), 5.71 (m, 1 H, H at C-2 of butene), 5.56 (s, 1 H, H at C-2 of dioxane), 4.24 (dd, J=11.5, 5.0 Hz, 2 H, H$^e$ at C-4 and C-6 of dioxane), 3.96 (m, 4 H, H at C-4 of butene and H$^a$ at C-4 and C-6 of dioxane), 3.53 (d, J=6.5 Hz, 2 H, H at C-1 of butene), 2.22 (m, 1 H, H$^a$ at C-5 of dioxane), 1.42 (d, J=13.5, 1 H, H at C-5 of dioxane) $^{13}$C NMR (CDCl$_3$, 125 MHz) δ 136.5, 134.9 (4° carbons of aromatic ring, 129.8, 129.0, 127.4, 126.7, 126.5, 126.4 (alkene and aromatic C-H's), 100.0 (C-2 of dioxane), 67.6 (C-4 and C-6 of dioxane), 35.2 (C-4 of alkene), 33.2 (C-1 of alkene), 25.8 (C-5 of dioxane) IR 2985, 2860 (aromatic C—H), 1100 (C—O) cm$^{-1}$; Mass Spec. (70 ev) m/z (rel abund 297 (M+-, 0.5), 217 (M+-Br, 86), 159 (M+-C$_3$H$_7$O and Br, 37), 143 (M+-C$_3$H$_7$O$_2$ and Br, 53), 131 (M+-1,3 dioxane and Br, 100); HRMS calcd for C$_{14}$H$_{16}$BrO$_2$: M+-H=297.0317. Found: 297.0340.

E. Preparation of [2-(2-butenyl)phenyl]-1,3-dioxanetriphenyl-phosphonium, bromide (14e)

Freshly prepared 14d (5.81 g; 19.57 mmol) was dissolved in benzene (50 ml) and a solution of triphenylphosphine (5.13 g; 19.57 mmol) in benzene (10 ml) added. A white precipitate began to form after 45 min. The solution was stirred for 48 h. A white precipitate was collected on a medium porosity frit and washed with anhydrous hexanes to give 14e (10.949 g; 89% yield). $^1$H NMR (CD$_3$OD, 500 MHz) δ 6.92–7.84 (m, 19 H, aromatic H of phosphine phenyls and 3,4,5 and 6), 5.90 (m, 1 H, H at C-3 of butene), 5.49 (s, 1 H, H at C-2 of dioxane), 5.38 (m, 1 H, H at C-2 of butene), 4.26 (dd, J=14.5, 7.5 Hz, 2 H, H at C-4 of butene), 3.91 (dd, J=11.0, 5.0 Hz, H$^e$ at C-4 and C-6 of dioxane), 3.78 (td, J=12.0, 2.0 Hz, 2 H, H$^a$ at C-4 and C-6 of dioxane), 3.48 (d, J=6.0 Hz, 2 H, H at C-1 of butene), 2.05 (m, 1 H, H$^a$ at C-5 of dioxane), 1.36 (d, J=13.5, 1 H, H$^e$ at C-5 of dioxane); $^{13}$C NMR (CDCl$_3$, 125 MHz) δ 141.2, 141.1 (4$^o$ carbons of aromatic ring), 137.0, 136.4, 133.7, 130.0, 129.7, 128.6, 126.6, 125.9, 118.5, 117.8 (alkene and aromatic C-H's), 100.4 (C-2 of dioxane), 66.9 (C-4 and C-6 of dioxane), 63.2 (C-4 of alkene), 34.9 (C-1 of alkene), 25.5 (C-5 of alkene); FABMS m/z (m-nitrobenzyl alcohol matrix) 480 (M+).

F. Preparation of tetrakis-1,2,4,5-penta-2,4-dienyl-5-[2(1.3-dioxanyl)-phenyl]benzene (14f)

To a suspension of 14e (9.8 g; 17.52 ml), potassium carbonate (2.66 g; 19.25 mmol) [pulverized in a mortar and heated gently in a bunsen burner flame], 18-crown-6 (231.5 mg; 0.876 mmol) in anhydrous THF (70 ml) was added and heated at reflux. Tetraformyl benzene (570 mg; 3 mmol) was added in 5 portions over 1 h. The yellow suspension turned green after an additional hour. The mixture was poured into a separatory funnel and washed with water. The organic phase was separated and set aside. The aqueous phase was extracted twice with ethyl acetate (100 ml). The combined organic phases were dried over magnesium sulfate. The crude mixture was evaporated onto Florisil and immediately subjected to column chromatography (silica gel; 20–30% ethyl acetate in hexanes). 14f was obtained as an unstable yellow-green semisolid. $^1$H NMR (CDCl$_3$, 500 MHz) δ 7.60–7.15 (m, 18 H, aromatic H), 6.80–5.80 (m, 16 H, olefinic H), 5.56 (s, 4 H, H at C-2 of dioxane), 4.15 (m, 8 H, H$^e$ at C-4 and C-6 of dioxanes), 3.84 (m, 8 H, H$^a$ at C-4 and C-6 of dioxanes), 3.55 (m, 8 H, H at C-1 of pentadienyls), 2.13 (m, 4 H, H$^a$ at C-5 of dioxanes), 1.30 (m, 4 H, H$^e$ at C-5 of dioxanes); $^{13}$C NMR (CDCl$_3$, 125 MHz) δ 137.6, 136.9, 135.9, 135.0, 130.8, 130.6, 129.9, 129.7, 129.0, 128.9, 127.7, 127.3, 126.5, 126.4, 126.3 (alkene and aromatic C-H's), 100.0 (C-2 of dioxanes), 67.4 (C-4 and C-6 of dioxanes), 35.8 (C-1 of pentadienyls), 25.7 (C-5 of pentadienyls); FABMS m/z (m-nitrobenzyl alcohol as matrix) 991 (M+).

G. Preparation of tetrakis-1,2,4,5-pentanyl-5-[2-(1,3-dioxanyl)phenyl]benzene (14g)

A Parr pressure bottle was charged with an ethyl acetate (25 ml) solution of triethylamine (1.0 ml) and 14f (2.59 g; 3.6 ml). Raney Nickel (thrice washed with water; ethanol and then ethyl acetate). The mixture was hydrogenated on the Parr at 50 psig. Over the course of the reaction, aliquots were removed and analyzed by $^1$H NMR. After each assay, fresh catalyst was added. Upon completion of the reaction, the solution was filtered through a celite pad to remove the catalyst. Column chromatography (25–35% ethyl acetate in hexanes) provided pure 14g (2.63 g, 100% yield). $^1$H NMR (CDCl$_3$, 500 MHz) δ 7.63 (dd, J=7.0, 1.5 Hz, 4 H, H at C-3), 7.24 (m, 8 H, H at C-4 and C-5), 7.17 (dd, J=7.0, 1.5 Hz, 4 H, H at C-6), 6.95 (s, 2 H, H at C-3 and C-6 of central benzene), 3.97 (td, J=12.0, 2.5 Hz, 8 H, H$^a$ at C-4 and C-6 of dioxanes), 2.75 (t, J=8.0 Hz, 8 H, H at C-5 of pentanyl chains), 2.60 (t, J=8.0 Hz, 8 H, H at C-1 of pentanyl chains), 2.24 (m, 4 H, H$^a$ at C-5 of dioxanes), 1.67 (overlapping peaks, J=8.0 Hz, 16 H, H at C-2 and C-4 of pentanyl chains), 1.52 (q, J=8.0, 8 H, H at C-3 of pentanyl chains), 1.40 (d, J=13.5 Hz, 4 H, H$^e$ at C-5 of dioxanes); $^{13}$C NMR (CDCl$_3$, 125 MHz) δ 140.7, 137.6 (4$^o$ C of aromatic rings), 136.2 (4$^o$ C of central benzene) 129.9, 129.4, 128.7, 126.2, 125.9 (aromatic C—H's), 99.8 (C-2 of dioxanes), 67.5 (C-4 and C-6 of dioxanes), 32.4 (C-5 and C-1 of pentanyl chains), 31.5, 31.4 (C-2 and C-4 of pentanyl chains), 29.9 (C-3 of pentanyl chains), 25.7 (C-5 of dioxanes).

H. Preparation of tetrakis-1,2,4,5-pentanyl-5-(2-formylphenyl)benzene (14h)

To a THF solution of 14g and 2,4-dinitrobenzaldehyde was added concentrated perchloric acid. The reaction was monitored by thin-layer chromatography on alumina.

I. Preparation of tetrakis(pentamethylene) capped porphyrin (14i)

A chloroform solution containing freshly distilled pyrrole and tetraaldehyde 14h was treated with boron trifluoride etherate. The reaction was monitored by UV-Vis analysis of aliquots that had been oxidized with DDQ. When the yield of porphyrinogen was maximized (3–7 h), chloranil was added and the mixture was heated at 65° C. for 2–3 h until the oxidation was complete as judged by UV-Vis spectrophotometry. The mixture was treated with a small amount of triethylamine and chromatographed on neutral alumina (25% chloroform/hexanes). The fastest moving red zone was then chromatographed on silica (40% chloroform/hexanes). UV maximum 419 μ.

We claim:

1. A synthetic catalyst for biological reactants which comprises:
   (a) two quasi-planar π-conjugated ring systems, each of which has an interfacial and extrafacial plane, and each of which is capable of chelating a transition metal ligand;
   (b) two transition metal ligands such as iron, manganese, copper, or cobalt, each of which is chelated by one of the ring systems;
   (c) at least two bridging units, each of which is covalently linked to the two ring systems, so that the ring systems are fixed to an interfacial plane separation in the range of about 4 to 7 angstroms; and
   (d) two capping groups, each of which is situated on the extrafacial plane side of one of the ring systems, and each of which is attached to the ring systems through at least one direct or indirect covalent linkage, so that extrafacial access to the ring systems for naturally occurring biological molecules is barred, wherein the ring systems are tetrapyrrole derivatives.

2. The catalyst of claim 1 wherein the tetrapyrrole derivatives are 5,10,15,20-tetrakis(phenyl)porphyrins.

3. The catalyst of claim 1 wherein the two transition metal ligands are selected from the group consisting of iron(III), manganese(III), copper(II) and combinations thereof.

4. The catalyst of claim 2 wherein the two transition metal ligands are selected from the group consisting of iron(III), manganese(III), copper(II) and combinations thereof.

5. The catalyst of claim 1 wherein the biological reactants are superoxide anion, hydroperoxide anion and hypochlorite anion.

6. The catalyst of claim 2 wherein the biological reactants are superoxide anion, hydroperoxide anion and hypochlorite anion.

7. The catalyst of claim 6 wherein the bridging units are covalently linked to the phenyl moieties of the ring systems.

8. The catalyst of claim 1 wherein the biological reactants are charged, and further comprising:
(e) one or more concentrating groups covalently linked to the bridging units, the concentrating groups possessing a charge opposing that of the biological reactants.

9. The catalyst of claim 8 wherein the tetrapyrrole derivatives are 5,10,15,20-tetrakis(phenyl)porphyrins.

10. The catalyst of claim 9 wherein the two transition metal ligands are selected from the group consisting of iron(III), manganese(III), copper(II) and combinations thereof.

11. The catalyst of claim 10 wherein the biological reactants are superoxide anion, hydroperoxide anion and hypochlorite anion.

12. The catalyst of claim 11 wherein the bridging units are covalently linked to the phenyl moieties of the ring systems.

13. The catalyst of claim 12 wherein the bridging units and concentrating groups together are —$CH_2$—N-R—$CH_2$—, wherein R is a positively charged concentrating group.

14. The catalyst of claim 13 wherein the positively charged concentrating group is a guanido group.

15. The catalyst of claim 14 having exactly four bridging units and concentrating groups, each bridging unit being covalently linked to a different phenyl moiety on the two ring systems.

16. The catalyst of claim 15 wherein the two transition metal ligands are iron(III).

17. The catalyst of claim 1 wherein the two capping groups are selected from the group consisting of aryl, cycloalkyl and aromatic heterocycles, and wherein each capping group is attached to a different ring system through at least one —$(CH_2)_n$— linkage, wherein n is an integer between 2 and 10.

18. The catalyst of claim 16 wherein the two capping groups are selected from the group consisting of phenyl, aryl, cycloalkyl and aromatic heterocycles, and wherein each capping group is attached to a different ring system through at least one —$(CH_2)_n$— linkage, wherein n is an integer between 2 and 10.

19. The catalyst of claim 18 wherein the two capping groups are phenyl groups, each phenyl group being attached to a different ring system through four —$(CH_2)_5$— linkages, wherein each linkage is attached to a different phenyl moiety on each ring system.

20. A pharmaceutical composition for the treatment of reactive oxidant tissue damage comprising an effective reactive oxidant-reducing amount of the catalyst of claim 1 and a pharmaceutically acceptable carrier.

21. A pharmaceutical composition for the treatment of reactive oxidant tissue damage comprising an effective reactive oxidant-reducing amount of the catalyst of claim 8 and a pharmaceutically acceptable carrier.

22. A pharmaceutical composition for the treatment of reactive oxidant tissue damage comprising an effective reactive oxidant-reducing amount of the catalyst of claim 11 and a pharmaceutically acceptable carrier.

23. A pharmaceutical composition for the treatment of reactive oxidant tissue damage comprising an effective reactive oxidant-reducing amount of the catalyst of claim 19 and a pharmaceutically acceptable carrier.

24. A method for the prevention and treatment of reactive oxidant tissue damage comprising administering to a patient in need of such treatment an effective amount of the composition of claim 20.

25. A method for the prevention and treatment of reactive oxidant tissue damage comprising administering to a patient in need of such treatment an effective amount of the composition of claim 21.

26. A method for the prevention and treatment of reactive oxidant tissue damage comprising administering to a patient in need of such treatment an effective amount of the composition of claim 22.

27. A method for the prevention and treatment of reactive oxidant tissue damage comprising administering to a patient in need of such treatment an effective amount of the composition of claim 23.

28. A method for the reduction of the level of cancer-causing oxygen species in a patient comprising administering to the patient an effective amount of the composition of claim 20.

29. A method for the reduction of the level of cancer-causing oxygen species in a patient comprising administering to the patient an effective amount of the composition of claim 21.

30. A method for the reduction of the level of cancer-causing oxygen species in a patient comprising administering to the patient an effective amount of the composition of claim 22.

31. A method for the reduction of the level of cancer-causing oxygen species in a patient comprising administering to the patient an effective amount of the composition of claim 23.

* * * * *